US012629001B2

(12) United States Patent
Kim et al.

(10) Patent No.: US 12,629,001 B2
(45) Date of Patent: May 19, 2026

(54) METHOD, APPARATUS AND SYSTEM FOR PROVIDING MEDICAL DIAGNOSIS ASSISTANCE INFORMATION BASED ON ARTIFICIAL INTELLIGENCE

(71) Applicant: VPIX Medical Incorporation, Daejeon (KR)

(72) Inventors: Kyuyoung Kim, Daejeon (KR); Kyungmin Hwang, Daejeon (KR)

(73) Assignee: VPIX MEDICAL INCORPORATION, Daejeon (KR)

( * ) Notice: Subject to any disclaimer, the term of this patent is extended or adjusted under 35 U.S.C. 154(b) by 47 days.

(21) Appl. No.: 18/533,869

(22) Filed: Dec. 8, 2023

(65) Prior Publication Data

US 2024/0188797 A1 Jun. 13, 2024

(30) Foreign Application Priority Data

Dec. 9, 2022 (KR) ........................ 10-2022-0171230
Dec. 9, 2022 (KR) ........................ 10-2022-0171231

(51) Int. Cl.
    A61B 1/00     (2006.01)
    A61B 1/04     (2006.01)
    A61B 1/06     (2006.01)
    G06T 7/00     (2017.01)
        (Continued)

(52) U.S. Cl.
    CPC ........ A61B 1/000096 (2022.02); A61B 1/043 (2013.01); A61B 1/063 (2013.01); A61B 1/0653 (2013.01); G06T 7/0012 (2013.01); G06T 7/11 (2017.01); G06T 11/00 (2013.01); G06T 2200/24 (2013.01); G06T 2207/10064 (2013.01); G06T 2207/10068 (2013.01); G06T

2207/20081 (2013.01); G06T 2207/30016 (2013.01); G06T 2207/30061 (2013.01);
        (Continued)

(58) Field of Classification Search
    None
    See application file for complete search history.

(56) References Cited

U.S. PATENT DOCUMENTS 7,848,572 B2    12/2010  Misawa
11,354,804 B1 *  6/2022  Behrooz .................. G06T 5/73
        (Continued)

FOREIGN PATENT DOCUMENTS

JP          4579759 B2      9/2010
JP        2019-525151 A     9/2019
        (Continued)

OTHER PUBLICATIONS

Office Action dated Feb. 16, 2023 in Korean Application No. 10-2022-0171230, in 20 pages.
        (Continued)

*Primary Examiner* — Katherine L Fernandez
(74) *Attorney, Agent, or Firm* — Knobbe, Martens, Olson & Bear, LLP

(57) ABSTRACT

Proposed is a method, apparatus, and system for providing medical diagnosis assistance information showing whether a tissue related to a tissue image is normal or abnormal (e.g., cancer) using the AI technology. Proposed are a method, an apparatus, and a system for training an AI model for producing medical diagnosis assistance information in consideration of conditions for obtaining a tissue image in an endomicroscope system for digital biopsy.

16 Claims, 20 Drawing Sheets

(51) Int. Cl.
    *G06T 7/11*          (2017.01)
    *G06T 11/00*       (2006.01)

(52) U.S. Cl.
    CPC ............... *G06T 2207/30081* (2013.01); *G06T 2207/30088* (2013.01); *G06T 2207/30096* (2013.01); *G06T 2207/30101* (2013.01); *G06T 2210/41* (2013.01)

(56) References Cited

U.S. PATENT DOCUMENTS

| | | | | |
|---|---|---|---|---|
| 2009/0003691 A1 * | 1/2009 | Padfield | ............... | G06V 20/695 |
| | | | | 382/164 |
| 2021/0169336 A1 * | 6/2021 | Sanchez | ............... | A61B 5/7264 |
| 2022/0172840 A1 | 6/2022 | Yamane et al. | | |
| 2024/0016387 A1 * | 1/2024 | Strasfeld | ............... | G06T 7/0012 |

FOREIGN PATENT DOCUMENTS

| | | | |
|---|---|---|---|
| JP | 2020-139842 A | 9/2020 | |
| JP | 2021-506003 A | 2/2021 | |
| KR | 10-1898220 B1 | 9/2018 | |
| KR | 10-2020-0100062 A | 8/2020 | |
| KR | 10-2192164 B1 | 12/2020 | |
| KR | 10-2246319 B1 | 5/2021 | |
| KR | 10-2347496 B1 | 1/2022 | |
| KR | 10-2022-0020284 A | 2/2022 | |
| KR | 10-2022-0109481 A | 8/2022 | |
| KR | 10-2022-0119669 A | 8/2022 | |
| WO | WO 2018/001689 A1 | 1/2018 | |
| WO | WO 2019/110561 A1 | 6/2019 | |

OTHER PUBLICATIONS

Office Action dated Feb. 16, 2023 in Korean Application No. 10-2022-0171231, in 14 pages.

Notice of Allowance dated Jun. 27, 2023 in Korean Application No. 10-2022-0171230, in 6 pages.

Office Action dated Jun. 28, 2023 in Korean Application No. 10-2022-0171231, in 16 pages.

* cited by examiner

MEDICAL DIAGNOSIS
ASSISTANCE
INFORMATION:CANCER

ACTUAL PATHOLOGIC
DIAGNOSIS:CANCER

MEDICAL DIAGNOSIS
ASSISTANCE
INFORMATION:NORMAL

ACTUAL PATHOLOGIC
DIAGNOSIS:NORMAL

MEDICAL DIAGNOSIS
ASSISTANCE
INFORMATION:CANCER

ACTUAL PATHOLOGIC
DIAGNOSIS:NORMAL

MEDICAL DIAGNOSIS
ASSISTANCE
INFORMATION:NORMAL

ACTUAL PATHOLOGIC
DIAGNOSIS:CANCER

FIG. 6A

DISSATISFIED WHEN IMAGE REGION SIZE REFERENCE
OF COLOR THRESHOLD IS NOT REACHED

FOR EXAMPLE, WHEN SIZE OF ACTIVATED REGION
AT SPECIFIC COLOR THRESHOLD IS LESS THAN SPECIFIC
RATIO TO ENTIRE REGION IN ACTIVATION MAP, DISPLAY
CONDITION IS NOT SATISFIED

Ex)

| | 255 | 150 | 30 |
|---|---|---|---|
| TP | | | |
| TP | | | |
| FP | | | |
| FP | | | |

FIG. 6B

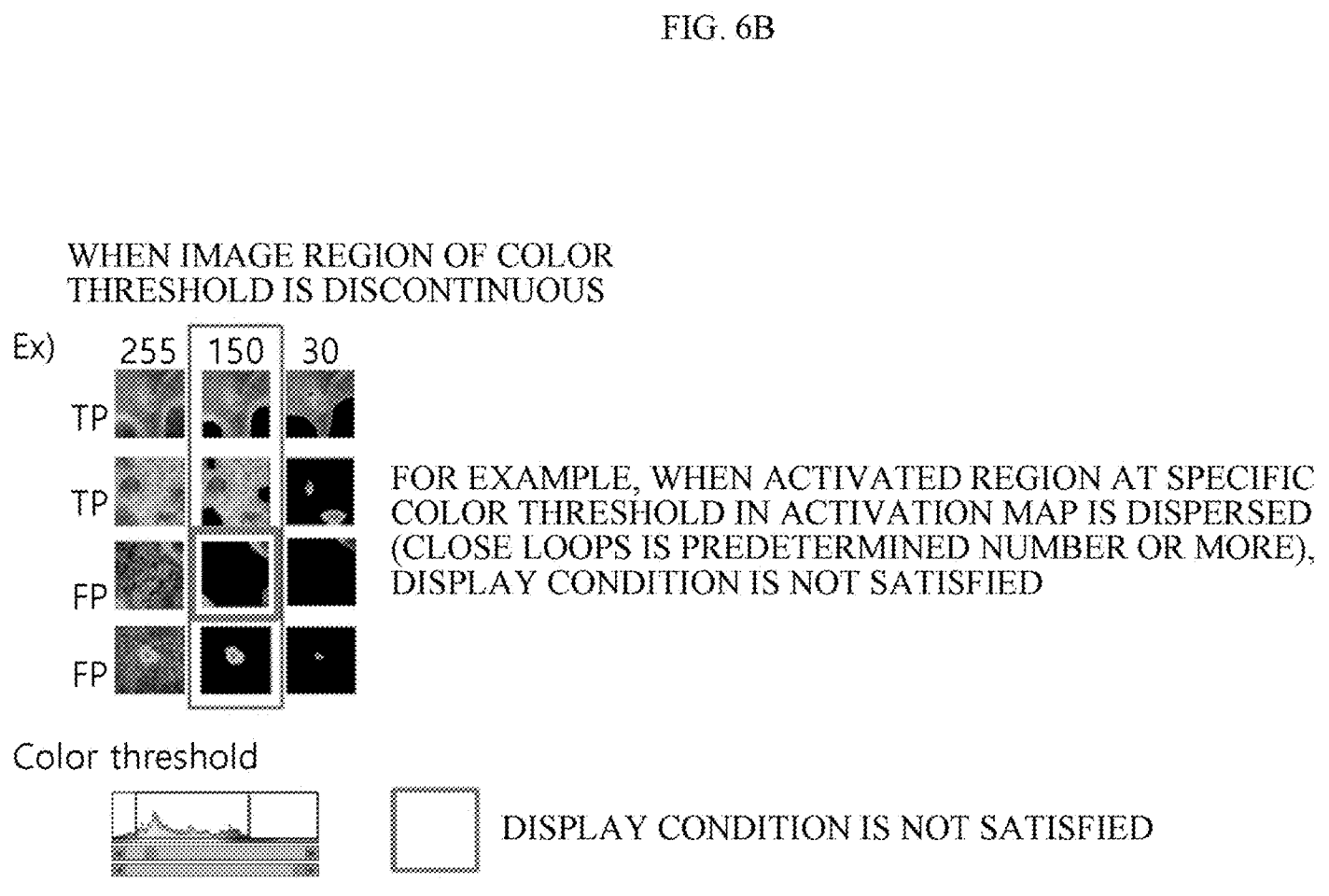

WHEN IMAGE REGION OF COLOR
THRESHOLD IS DISCONTINUOUS

FOR EXAMPLE, WHEN ACTIVATED REGION AT SPECIFIC
COLOR THRESHOLD IN ACTIVATION MAP IS DISPERSED
(CLOSE LOOPS IS PREDETERMINED NUMBER OR MORE),
DISPLAY CONDITION IS NOT SATISFIED

DISPLAY CONDITION IS NOT SATISFIED

Ex)      255      150      30

TP

TP

FP

FP

Color threshold

TISSUE IMAGE IS OBTAINED — 801

PART INFORMATION IS CHECKED — 802

NUMBER OF SPECIFIC IMAGES CORRESPONDING TO BODY PART IS CHECKED — 803

TISSUE IMAGE WAS OBTAINED BY NUMBER OF SPECIFIC IMAGES? — 804

N

Y

MEDICAL DIAGNOSIS ASSISTANCE INFORMATION IS PRODUCED — 805

FIG. 9

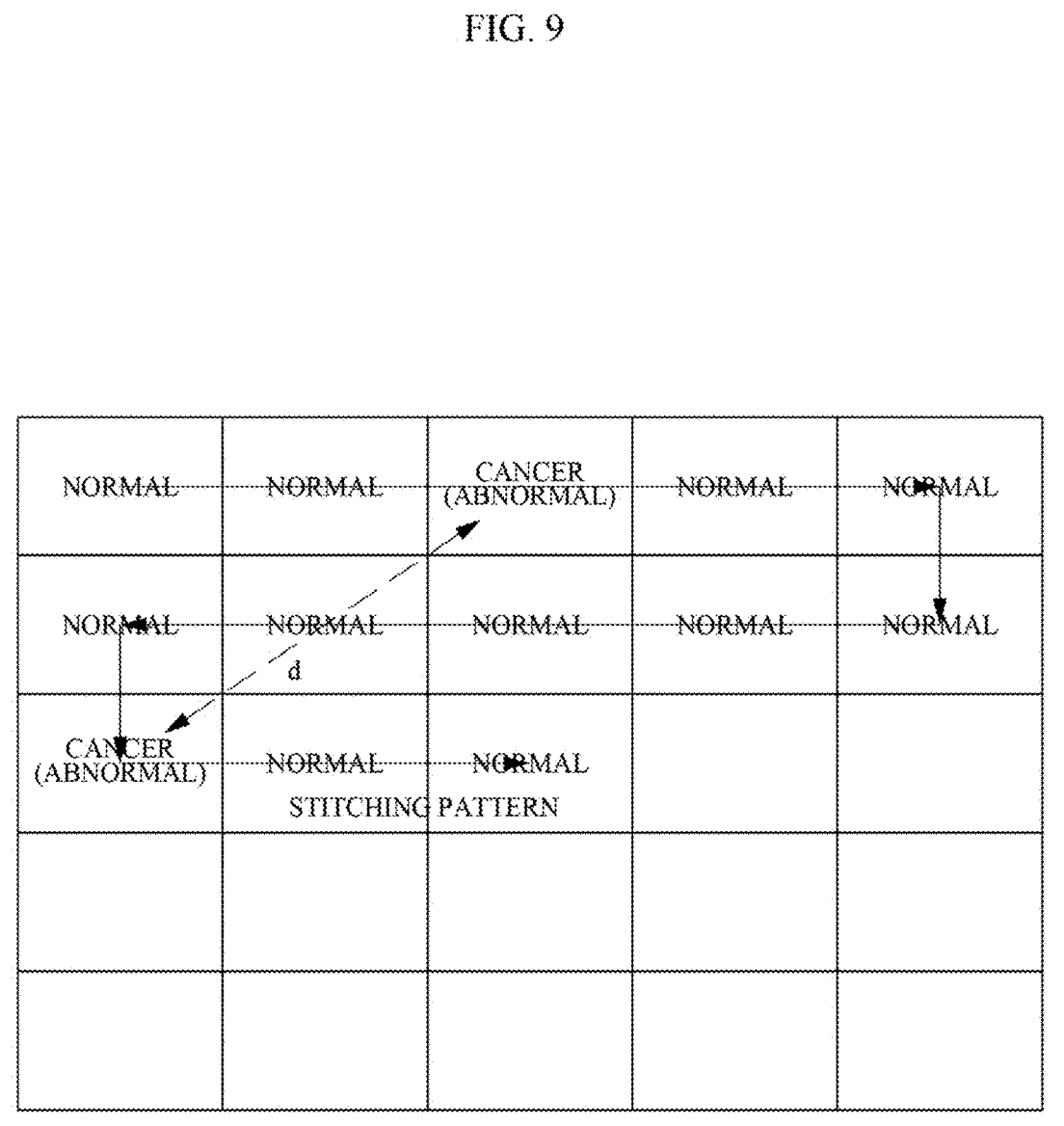

| | | | | |
|---|---|---|---|---|
| NORMAL | NORMAL | CANCER (ABNORMAL) | NORMAL | NORMAL |
| NORMAL | NORMAL | NORMAL | NORMAL | NORMAL |
| CANCER (ABNORMAL) | NORMAL | NORMAL | | |
| | | | | |
| | | | | | d

STITCHING PATTERN

FIG. 15A

| | 1 stain | | 2 stain |
|---|---|---|---|
| | CYTOPLASM | CELL NUCLEUS | |
| FIRST WAVELENGTH (ONE LIGHT SOURCE) | AI MODEL 1-1 | AI MODEL 1-2 | AI MODEL 2 |
| SECOND WAVELENGTH (TWO LIGHT SOURCES) | AI MODEL 3-1 | AI MODEL 3-2 | AI MODEL 4 |

METHOD, APPARATUS AND SYSTEM FOR PROVIDING MEDICAL DIAGNOSIS ASSISTANCE INFORMATION BASED ON ARTIFICIAL INTELLIGENCE

CROSS REFERENCE TO RELATED APPLICATION

The present application claims priority to Korean Patent Applications No. 10-2022-0171230, filed Dec. 9, 2022 and No. 10-2022-0171231, filed Dec. 9, 2022 the entire contents of which are incorporated herein for all purposes by this reference.

BACKGROUND

Technical Field

The present disclosure relates to a method, apparatus, and system for providing medical diagnosis assistance information that medical technicians can refer to in order to make pathological diagnoses.

Description of Related Technology

In the medical field, a biopsy that takes cells or tissues from a body and observes them through an endomicroscope is performed to make accurate diagnoses of diseases such as cancer. According to a frozen section biopsy that is an example of biopsy, a medical technician makes a pathologic slide by freezing and staining tissues taken from a human body and observes the pathologic slide through an endomicroscope, thereby performing a pathologic diagnosis on the tissues.

SUMMARY

According to the AI technology, AI models can learn a great amount of learning data (e.g., images) in advance and can output specific judgments or estimation results on input data with high accuracy.

When an AI model is trained a great amount of tissue images in advance and a tissue image to be observed is input to the AI model, the AI model can output medical diagnosis assistance information showing whether the cells or tissues in the tissue image are normal or abnormal (e.g., cancer).

Meanwhile, AI models only output medical diagnosis assistance information as the result of inference on the input tissue image and do not determine whether the medical diagnosis assistance information is effective information that can be used for pathologic diagnosis. When an AI model outputs ineffective medical diagnosis assistance information and the medical diagnosis assistance information is provided to a medical technician, it may cause incomplete judgment of the medical technician. Accordingly, it is required to design a method of providing medical technicians with only effective information that can be actually used for pathologic diagnosis in medical diagnosis assistance information output by AI models.

Further, an endomicroscope system for digital biopsy can obtain tissue images in accordance with specific conditions, such as the wavelength band of a laser, parts of cells or tissues, etc. AI models can learn, in advance, tissue images obtained through an endomicroscope system and can output medical diagnosis assistance information for the input tissue images. Accordingly, it is required to consider conditions, under which tissue images were obtained, in learning of AI models so that the AI models can output more accurate medical diagnosis assistance information.

Further, endomicroscope systems for digital biopsy do not need a pathologic slide using H&E staining. Accordingly, the types of tissue images obtained through such endomicroscope systems may be different from H&E images familiar to medical technicians.

When it is possible to convert a tissue image obtained through such an endomicroscope system into an image similar to the staining type of an H&E image and then provide the converted image to a medical technician, the medical technician would be able to conveniently perform pathologic diagnosis with reference to an image having a type similar to himself/herself. Accordingly, it is required to design an AI model for pseudo coloring that converts images obtained through endomicroscope systems for digital biopsy to be close to the staining type of H&E images.

Further, when pseudo coloring is performed on an image of a specific tissue, there is an expected staining type depending on whether the specific tissue is normal or abnormal (e.g., cancer). When a suitable pseudo coloring AI model can be selected in accordance with whether a tissue is normal or abnormal (e.g., cancer), it would be possible to obtain a pseudo-coloring resultant image (e.g., which may be referred to as a virtual H&E image or an H&E similar image) closer to an actual H&E image through the selected AI model. Accordingly, it is required to select an AI model for pseudo coloring in consideration of the diagnosis result of tissues.

One aspect is a method, apparatus, and system for providing medical diagnosis assistance information showing whether a tissue related to a tissue image is normal or abnormal (e.g., cancer) using the artificial intelligence (AI) technology.

Another aspect is a method of training an AI model for providing medical diagnosis assistance information in consideration of conditions under which a tissue image is obtained.

Another aspect is an AI-based pseudo coloring method, apparatus, and system.

Another aspect is a method, apparatus, and system for generating an image similar to the type (e.g., color) of hematoxylin & eosin staining by inputting a tissue image obtained through an endomicroscope system into an AI model for pseudo coloring.

Another aspect is a confocal fluorescence endomicroscope system that includes: a laser scanner; a light receiver; and a processor, wherein the processor is configured to: generate a first driving signal corresponding to a first axis and a second driving signal corresponding to a second axis different from the first axis; generate a first image to detect excitation light generated by light emitted to a tissue from an end of the laser scanner operating based on the first driving signal and the second driving signal; identify an activated region related to the medical diagnosis assistance information on the first image by inputting the first image into an artificial intelligence model; determine whether at least one of the size of the activated region or the number of closed loops satisfies a predetermined condition; provide the medical diagnosis assistance information on the first image when the condition is satisfied; and not to provide the medical diagnosis assistance information on the first image when the condition is not satisfied.

Another aspect is an apparatus, and a system for training an AI model for providing medical diagnosis assistance information in consideration of conditions for obtaining a tissue image in an endomicroscope system for digital biopsy.

Another aspect is a confocal fluorescence endomicroscope system that includes: a laser scanner; a light receiver; and a processor, wherein the processor is configured to: generate a first driving signal corresponding to a first axis and a second driving signal corresponding to a second axis different from the first axis; control the light receiver to sense excitation light generated by light emitted to a tissue from an end of the laser scanner operating based on the first driving signal and the second driving signal; generate a first image related to a tissue based on the detected excitation light; and identify medical diagnosis assistance information including information on the image by inputting a wavelength value of the light, organ information of the tissue, and the first image into a first artificial intelligence model for cancer diagnosis, wherein first artificial intelligence model is trained based on a wavelength value of light, organ information of a tissue, and a plurality of images of the tissue.

Another aspect is an AI-based pseudo-coloring method, apparatus, and system that generates a tissue image obtained through an endomicroscope system for digital biopsy into an image similar to the staining type of an H&E image.

Another aspect is a confocal fluorescence endomicroscope system that includes: a laser output module; a laser scanner; a light receiver; and a processor, wherein the processor is configured to: generate a first driving signal corresponding to a first axis and a second driving signal corresponding to a second axis different from the first axis; control the light receiver to detect excitation light generated by light emitted to a tissue from an end of the laser scanner operating based on the first driving signal and the second driving signal; generate a first image related to a tissue based on the detected excitation light; identify (1) staining information of the issue, (2) operation information of the laser output module, and (3) organ information of the tissue; and generate a first H&E image corresponding to the first image by inputting the first image, the dye information, the operation information, and the organ information into a first artificial intelligence model for generating a virtual H&E image, wherein the first artificial intelligence model is trained based on a plurality of items of staining information, a plurality of items of operation information of the laser output module, a plurality of images of the tissue, and a plurality of H&E images of the tissues.

Another aspect is a method, apparatus, and system for providing medical diagnosis assistance information showing whether a tissue related to a tissue image is normal or abnormal (e.g., cancer) using the AI technology. Accordingly, medical diagnosis assistance information that can be actually used for pathologic diagnosis can be provided to medical technicians and the medical technicians can perform more accurate and quick pathologic diagnosis based on the provided medical diagnosis assistance information.

Another aspect is a method, an apparatus, and a system for training an AI model for producing medical diagnosis assistance information in consideration of conditions for obtaining a tissue image in an endomicroscope system for digital biopsy. Accordingly, it is possible to obtain an AI model that generates more accurate medical diagnosis assistance information for a tissue image that is an observation object.

Another aspect is an AI-based pseudo-coloring method, apparatus, and system that generate a tissue image obtained through an endomicroscope system for digital biopsy into an image similar to the staining type of an H&E image. Accordingly, medical technicians who use an endomicroscope system can be provided in real time with tissue images similar to the staining type of an H&E image and can perform quick and accurate pathologic diagnosis based on the tissue images.

The aspects and effects of the disclosure are not limited to those described above and other aspects and effects can be clearly understood by those skilled in the art from the following description.

BRIEF DESCRIPTION OF THE DRAWINGS

Drawings for embodiments are briefly introduced to more clearly explain the technical plans of the embodiments of the present disclosure. The following drawings are only references for embodiments of the present disclosure without limiting the present disclosure.

FIG. 6A and FIG. 6B are diagrams showing an example of display conditions of medical diagnosis assistance information according to an embodiment of the present disclosure.

FIG. 9 is a diagram showing a method of providing medical diagnosis assistance information in a specific environment according to an embodiment of the present disclosure.

FIG. 15A and FIG. 15B are diagrams showing an example of selecting an AI model for pseudo coloring in accordance with conditions for obtaining a tissue image through an endomicroscope system according to an embodiment of the present disclosure.

Figure 16:
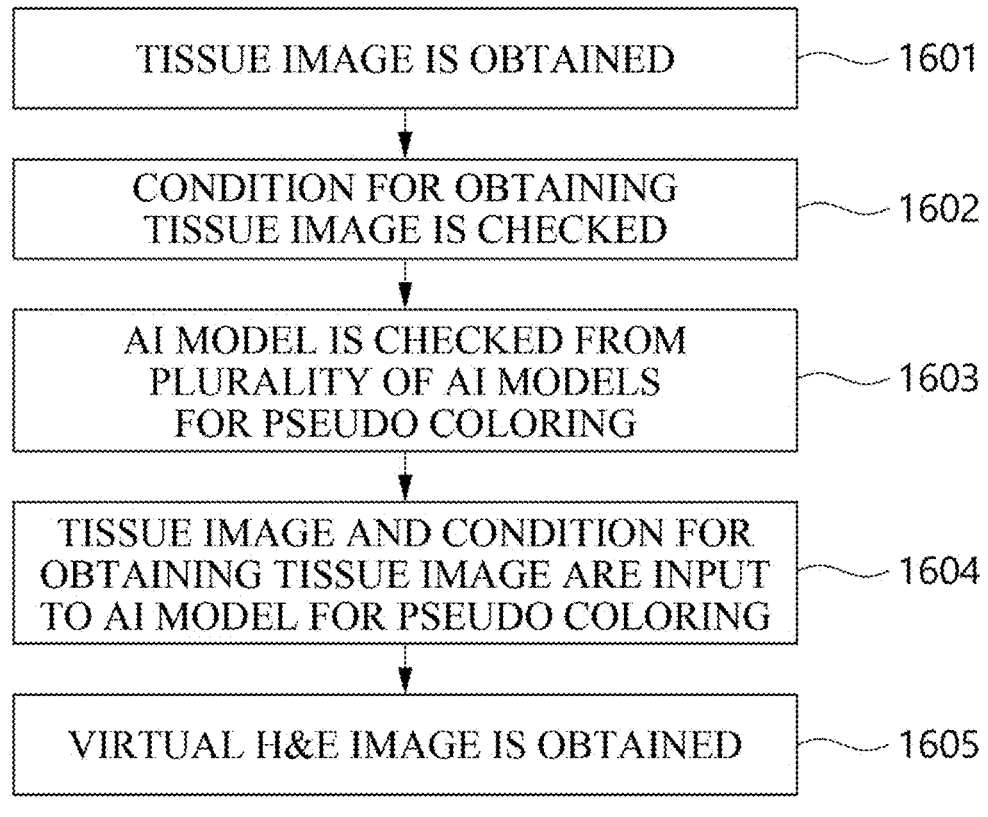

FIG. 16 is a diagram showing a method of selecting an AI model for pseudo coloring in accordance with conditions for obtaining a tissue image through an endomicroscope system according to an embodiment of the present disclosure.

DETAILED DESCRIPTION

In general, when observing a tissue section without staining cells or tissues, it is difficult to determine the structure, so tissues are stained using dyes that selectively bond to specific cells, organelles, extracellular matrixes, etc. As an example of histochemical stains, Hematoxylin & Eosin staining that uses two dyes of Hematoxylin and Eosin is generally used. Hematoxylin, which is a blue basic dye having a positive charge, stains nuclei blue, has a lot of DNA and RNA having a negative charge, in cells. Eosin, which is a red acid dye having a negative charge, usually stains cytoplasm red by bonding to protein having a positive charge in cells. Medical technicians make a pathologic slide by staining tissues taken from a body in accordance with H&E staining and perform pathologic diagnosis on the tissues with reference to an H&E image obtained by observing the pathologic slide through an endomicroscope.

However, the existing biopsy has a problem that it takes long time to make a pathologic slide for observation through an endomicroscope, a sampling error related to parts is generated, etc., so the accuracy is low.

Recently, a digital biopsy technology that immediately generates an image for pathologic diagnosis by staining tissues by applying specific dyes (e.g., a fluorescent dye) and then scanning the tissues without making a pathologic slide has been developed.

Accordingly, medical technicians can be provided a tissue image in real time through an endomicroscope system for digital biopsy and can perform pathologic diagnosis on corresponding tissues.

Nevertheless, it takes medical technicians long time to make pathologic diagnoses by observing a large number of tissue images one by one and there is a possibility of wrong diagnoses due to incomplete judgment by medical technicians. Further, actual medical facilities may have limitations, for example, medical facilities may not be equipped with pathologic infrastructures, may not have a department of pathology to which medical technicians who perform pathologic diagnoses pertain, or it is difficult to perform pathologic diagnosis and share the results in the hours excluding the hours for pathology.

Accordingly, there is a need for plans that can provide convenience for medical technicians in pathologic diagnosis and can minimize the possibility of wrong diagnosis.

The objectives, features, and advantages of the present disclosure will be made clearer through the following detailed description related to the accompanying drawings. However, the present disclosure may be modified in various ways and implemented by various exemplary embodiments, so that specific exemplary embodiments are shown in the drawings and will be described in detail hereafter.

In the drawings, the thicknesses of layers and regions are exaggerated for clarity, and when a component or a layer is "on" another component or layer, it includes all cases in which the component or layer is not only on another component or layer and another layer or component is disposed therebetween. Like reference numerals fundamentally indicate the same components throughout the specification. Further, components having functions within the range of the same spirit shown in the drawings related to embodiments, respectively, are given the same reference numerals.

Detailed descriptions of well-known functions or configurations related to the present disclosure will not be provided so as not to unnecessarily obscure the description of the present disclosure. Further, numbers (e.g., first, second, etc.) used in the description of the present disclosure are only identification symbols to discriminate one component from another component.

Further, terms "module" and "unit" that are used for components in the following description are used only for the convenience of description without having discriminate meanings or functions.

In the present disclosure, an "AI model" may include a hardware structure that is specified to train data (e.g., images) and perform inference, such as specific judgment or estimation, on input data, and may include a software structure additionally or substitutionally other than a hardware structure.

Further, in the present disclosure, a "tissue image" may mean an image obtained through an endomicroscope system for pathologic diagnosis and may be referred to as a bio-image, a pathologic image, or terms having same/similar meanings.

A method according to an embodiment of the present disclosure may be implemented in a program that can be executed by various computers, and may be recorded on computer-readable media. The computer-readable media may include program commands, data files, and data structures individually or in combinations thereof. The program commands that are recorded on the media may be those specifically designed and configured for the present disclosure or may be those available and known to those engaged in computer software in the art. The computer-readable recording media include magnetic media such as hard disks, floppy disks, and magnetic media such as a magnetic tape, optical media such as CD-ROMs and DVDs, magneto-optical media such as floptical disks, and hardware devices specifically configured to store and execute program commands, such as ROM, RAM, and flash memory. The program commands include not only machine language codes compiled by a compiler, but also high-level language code that can be executed by a computer using an interpreter etc. The hardware device may be configured to operate as one or more software modules to perform the operation of the present disclosure, and vice versa.

According to an embodiment of the present disclosure, there is provided a method, apparatus, and system for providing medical diagnosis assistance information showing whether a tissue related to a tissue image is normal or abnormal (e.g., cancer) using the AI technology. According to an aspect, there may be a provided a confocal fluorescence endomicroscope system that includes a laser scanner, a light receiver, and a processor in which the processor is configured to generate a first driving signal corresponding to a first axis and a second driving signal corresponding to a second axis different from the first axis, to generate a first image to detect excitation light generated by light emitted from an end of the laser scanner operating based on the first driving signal and the second driving signal, to identify activated regions related to medical diagnosis assistance information on the first image by inputting the first image into an artificial intelligence model, to determine whether at least one of the size of the activated regions and the number of closed loops satisfies a predetermined condition, to provide the medical diagnosis assistance information on the first image when the condition is satisfied, and to not provide medical diagnosis assistance information on the first image when the condition is not satisfied.

Further, the processor may be set to determine that the condition is not satisfied in at least one case of the case (1) when the size of the activated region at a specific color threshold is less than a threshold in the entire region or the case (2) when the number of the closed loops of the activated region is a predetermined number or more.

Further, the specific color threshold may be a pre-designated value or a value selected by a user.

Further, the processor may be set to determine that the condition is satisfied (1) when the size of the activated region at a specific color threshold is a threshold or more in the entire region and (2) when the number of the closed loops of the activated region is less than a predetermined number.

Further, the processor may be configured to transmit the first image to an external device such that the external device displays the medical diagnosis assistance information on the first image when the condition is satisfied.

Further, the light may include first light having a first wavelength and second light having a second wavelength and the processor may be set to generate a first assistant image about the tissue using the first light, generate a second assistant image about the tissue using the second light, generate the first image by combining the first assistant image and the second assistant image, and determine final medical diagnosis assistance information on the tissue using first medical diagnosis assistance information obtained by inputting the first assistant image into the artificial intelligence model, second medical diagnosis assistance information obtained by inputting the second assistant image into the AI model, and third medical diagnosis assistance information obtained by inputting the first image into the artificial intelligence model.

Further, the first wavelength may be included in one wavelength band of 400 to 410 nm, 480 to 500 nm, or 770 to 880 nm and the second wavelength may be included in another wavelength band different from the wavelength band including the first wavelength.

Further, the processor may be set to identify organ information on the tissue, identify the number of specific images corresponding to the organ information, and determine medical diagnosis assistance information on the tissue using a plurality of images of the tissue when the plurality of images is obtained by the number of the specific images.

Further, the processor may be set to identify medical diagnosis assistance information on each of the plurality of images when the plurality of images is obtained by the number of the specific images while moving a probe including the laser scanner along a predetermined pattern, and to output a message that ignores medical diagnosis assistance information on one or more images, which relate to first type of medical diagnosis assistance information of the medical diagnosis assistance information on each of the plurality of images, or requests new medical diagnosis assistance information on the one or more images, when the number of the one or more images is a predetermined number or less and the minimum distance between the one or more images exceeds a predetermined distance.

Further, according to an embodiment of the present disclosure, there is provided a method, an apparatus, and a system for training an AI model for producing medical diagnosis assistance information in consideration of conditions for obtaining a tissue image in an endomicroscope system for digital biopsy.

According to an aspect, there may be provided a confocal fluorescence endomicroscope system that includes a laser scanner, a light receiver, and a processor in which the processor is configured to generate a first driving signal corresponding to a first axis and a second driving signal corresponding to a second axis different from the first axis, control the light receiver to detect excitation light generated by light emitted from an end of the laser scanner operating based on the first driving signal and the second driving signal, generate a first image about a tissue based on the detected excitation light, and identify medical diagnosis assistance information on the image by inputting a wavelength value of the light, organ information of the tissue, and the first image into a first artificial intelligence model for cancer diagnosis; and the first artificial intelligence model is trained based on the wavelength value of the light, the organ information of the tissue, and a plurality of images of the tissue.

Further, the confocal fluorescence endomicroscope system further includes a laser output module and the processor may identify the organ information of the tissue and the number of cell nuclei in the first image and may identify light output intensity of the laser output module by inputting the organ information and the number of the cell nuclei into a second artificial intelligence model. The second artificial intelligence model can be trained based on the organ information of the tissue, the number of the cell nuclei, and the light output intensity of the laser output module, and may be set to generate a second image of the tissue by operating the laser output module at the identified light output intensity.

According to an embodiment of the present disclosure, there are provided an AI-based pseudo-coloring method, apparatus, and system that generate a tissue image obtained through an endomicroscope system for digital biopsy into an image similar to the staining type of an H&E image. According to an aspect, thereby may be provided a confocal fluorescence endomicroscope system that includes a laser output module, a laser scanner, a light receiver, and a processor in which the processor is configured to generate a first driving signal corresponding to a first axis and a second driving signal corresponding to a second axis different from the first axis, control the light receiver to detect excitation light generated by light emitted from an end of the laser scanner operating based on the first driving signal and the second driving signal, generate a first image of a tissue based on the detected excitation light, identify (1) staining information of the tissue, (2) operation information of the laser output module, and (3) organ information of the tissue, and generate a first H&E image corresponding to the first image by inputting the first image, the staining information, the operation information, and the organ information into a first artificial intelligence model for generating a virtual H&E image; and the first artificial intelligence model is trained based on staining information of each of a plurality of tissues, a plurality of items of operation information of the laser output module, a plurality of images of the plurality of tissues, respectively, and an H&E image of each of the plurality of tissues.

Further, the first image may be a grayscale image or a red green blue (RGB) color image in images obtained in a focused state.

Further, the staining information of the tissue may include at least one of first staining information on whether at least one of cell nuclei or cytoplasm in the tissue is stained or second staining information on a fluorescent dye staining the tissue.

Further, the second staining information may include information on at least one of PpIX (5-ALA), Hoechst, DAPI, Acridine orange (AO), Fluorescein Sodium (FNa), Fluorescein isothiocyanate (FITC), Propidium iodide, acriflavine, Indocyanine Green (ICG), Pafolacianine, and Methylene Blue (MB).

Further, the operation information of the laser output module may include at least one of information on first light having a first wavelength and second light having a second wavelength.

Further, the first wavelength may be included in one wavelength band of 400 to 410 nm, 480 to 500 nm, or 770 to 800 nm and the second wavelength may be included in another wavelength band of the wavelength bands.

Further, the first artificial intelligence model may be further trained based on personal information of examinees, the personal information may include body information, sex information, or age information, and the processor may be set to generate the first H&E image by additionally inputting the personal information of an examinee corresponding to the tissue into the first artificial intelligence model.

Further, the processor may be set to select one of a first mode or a second mode for generating a virtual H&E image, generate the first H&E image using the first artificial intelligence model when the selected mode is the first mode, identify medical diagnosis assistance information on the first image by inputting the first image into an artificial intelligence model for cancer diagnosis when the selected mode is the first mode, generate a second H&E image by inputting the first image into the second artificial intelligence model when the medical diagnosis assistance information on the first image shows abnormality, and generate a third H&E image by inputting the first image into the third artificial intelligence model when the medical diagnosis assistance information on the second image shows normality; and the second artificial intelligence model and the third artificial intelligence model each may be in associated with one of pix-2-pix, cycle generative adversarial network (GAN), style GAN algorithms.

Further, there may be provided a confocal fluorescence endomicroscope system in which the processor is configured to select one of a first mode or a second mode for generating a virtual H&E image, generate the first H&E image using the first artificial intelligence model when the selected mode is the first mode, identify (1) first staining information of the tissue (e.g., which may show whether at least one of a cell nuclei or cytoplasm is stained) and (2) first operation information of the laser output module (e.g., which may show there is a short-wavelength or long-wavelength light source) when the selected mode is the second mode, select a specific artificial intelligence model from a plurality of artificial intelligence models for generating a virtual H&E image based on the first staining information and the first operation information (in this case, the plurality of AI models may be different from each other), identify second staining information (e.g., dye information) of the tissue and second operation information (e.g., wavelength information) of the laser output module, and generate a second H&E image corresponding to the first image by inputting the first image, the second staining information, and the second operation information into the specific artificial intelligence model; and the specific artificial intelligence model is trained based on staining information of each of a plurality of tissues, information on a plurality of wavelength values of the laser output module, images of the plurality of tissues, respectively, and an H&E image of each of the plurality of tissues.

Further, the processor may be set to identify an activated region of the first image and generate the first H&E image by gradually enlarging a color conversion from the activated region.

In the medical field, a biopsy that takes cells or tissues from a body and observes them through an endomicroscope is performed to make accurate diagnoses of diseases such as cancer. According to a frozen section biopsy that is an example of biopsy, a medical technician makes a pathologic slide by freezing and staining a tissue taken from a human body and observes the pathologic slide through an endomicroscope, thereby performing pathologic diagnosis on the tissue.

In general, when observing a tissue section without staining cells or tissues, it is difficult to determine the structure, so tissues are stained using dyes that selectively bond to specific cells, organelles, extracellular matrixes, etc. As an example of histochemical stains, Hematoxylin & Eosin staining that uses two dyes of Hematoxylin and Eosin is generally used. Hematoxylin, which is a blue basic dye having a positive charge, stains nuclei bule, which has a lot of DNA and RNA having a negative charge, in cells. Eosin, which is a red acid dye having a negative charge, usually stains cytoplasm red by bonding to protein having a positive charge in cells. Medical technicians make a pathologic slide by staining tissues taken from a body in accordance with H&E staining and perform pathologic diagnosis on the tissues with reference to an H&E image obtained by observing the pathologic slide through an endomicroscope.

However, the existing biopsy has a problem that it takes long time to make a pathologic slide for observation through an endomicroscope and accuracy is low such as a sampling error for parts.

Recently, a digital biopsy technology that immediately generates an image for pathologic diagnosis by staining a tissue by applying a specific dye (e.g., a fluorescent dye) and then scanning the tissue without making a pathologic slide has been developed.

Accordingly, medical technicians can be provided with a tissue image in real time through an endomicroscope system for digital biopsy and can perform pathologic diagnosis on the corresponding tissue.

In the present disclosure, an endomicroscope system for digital biopsy may include an image generating device and the image generating device may be an optical device for obtaining and providing at least one of a reflected image (RI) a fluorescence image (FI), and a transmitted image (TI) of an object in real time.

For example, an endomicroscope system may include various kinds of endomicroscopes for directly observing or diagnosing pathologic states of living bodies.

The endomicroscope may mean an optical endomicroscope based on a laser such confocal, two-photon, and OCT.

In general, a confocal endomicroscope performs imaging in the unit of pixel by focusing only light, which has passed through a pinhole, on an object lens while blocking nonfocused light using a pinhole.

As one of endomicroscopes that uses such a confocal principle, there is a confocal laser scanning endomicroscope (CLSM) that applies a laser to a specimen, generates light of a predetermined wavelength, receives only accurately focused light, and converts the light into a digital signal, thereby performing observation.

The CLSM, unlike common optical endomicroscopes, focuses a laser beam on a specimen and can generate an image using fluorescent light, reflected light, and transmitted light generated from the specimen.

For example, it is possible to observe a fluorescence image by using autofluorescence generated from a specific substance in a specimen or injecting a fluorescent substance into a specimen.

Further, when a CLSM is used, diffused light coming out of other parts of a specimen is blocked, so it is possible to obtain an image that is very clear and has high resolution.

As another example, an endomicroscope system may include a laser microscanner for precisely observing or diagnosing an object in real time.

Laser microscanners may be, representatively, classified into a micro electric mechanical system (MEMS) scanner using a semiconductor processing method and an optical fiber scanner using optical fibers.

Further, laser microscanners can be classified into a side-viewing type, a circumferential-viewing type, and a forward-viewing type.

There are a mirror scanner, a lens scanner, etc. that reflect laser light as MEMS scanners and MEMS scanners usually perform side imaging.

MEMS scanners additionally require a device for taking again a picture of a beam bent by a mirror for forward imaging, so there is a defect that compact packaging is difficult.

However, an optical fiber scanner is driven using an actuator, such as a piezoelectric elements, so there is an advantage that packaging is simple and compact packaging is possible in comparison to a MEMS mirror scanner.

Further, since an optical fiber scanner is driven at the resonance frequency of optical fibers, there is an advantage that a field of view (FOV) is implemented at a relatively low voltage.

The endomicroscope system described above can be used in various fields for obtaining a fluorescence image, a reflected image, a transmitted image, etc. of an object as 2D or 3D images.

For example, an endomicroscope system may be used to observe images of an object and make diagnoses in real time in fields such as biological studies, disease diagnosis, endoscopic surgeries, etc. Further, an endomicroscope system can be used to measure the remaining lifespan of examination target metal structures based on cracks, holes, and the degree of creep of metal facilities. Further, an endomicroscope system can be applied also to a LiDAR device that generates 3D information by measuring a returning light distance by reflecting and distributing a laser beam.

Figure 1:
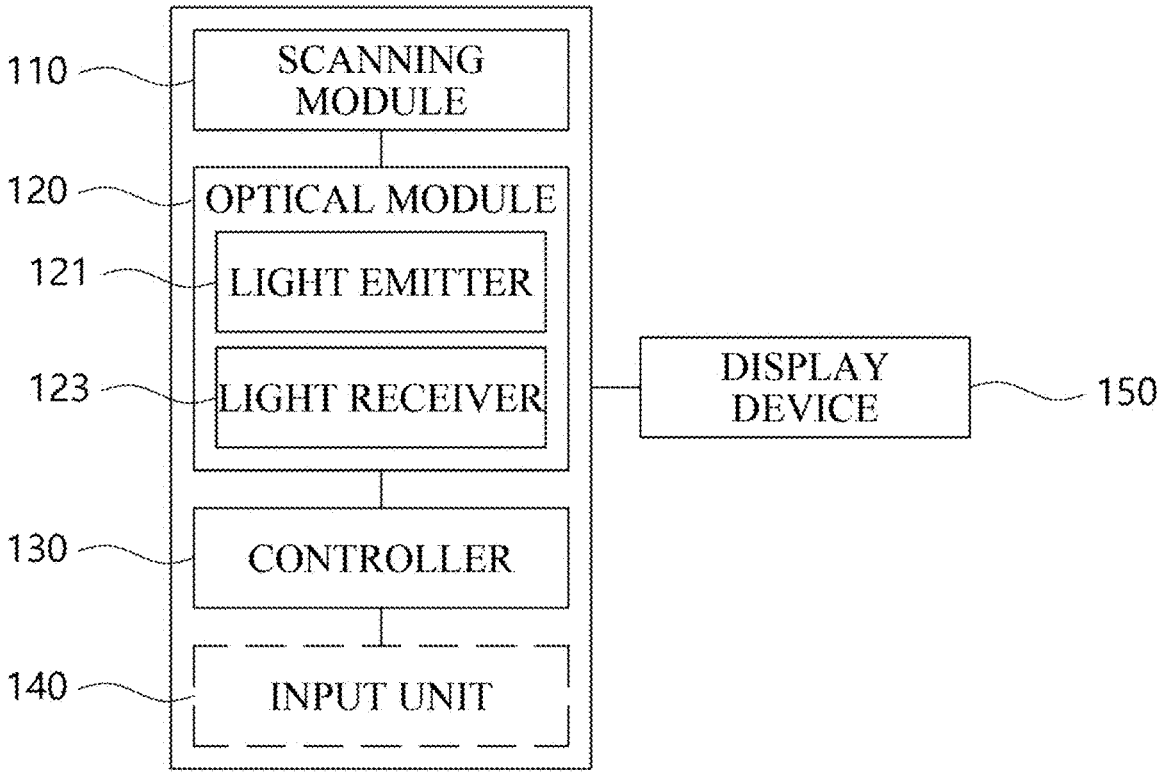
FIG. 1 is a diagram showing an endomicroscope system according to an embodiment of the present disclosure.

FIG. 1 is a diagram showing an endomicroscope system according to an embodiment of the present disclosure.

Referring to FIG. 1, an endomicroscope system may include a scanning module 110, a controller 130, and an optical module 120.

The scanning module 110 can emit light to an object in contact with or at a predetermined distance from the object. Accordingly, the scanning module 110 can measure the inside within a preset distance from the surface of the object. For example, the preset distance can be changed by adjusting the focal distance of a lens module to be described below and may be 0 um to 250 um.

Further, the scanning module 100 may be a fixed device or a handheld type of device. For example, when the scanning module 110 is a handheld type, it may be an optical device of an endoscope, pen, or the like type. For example, when the scanning module 110 is a handheld type, it may be implemented in the types of an endoscope, a pen, etc.

The scanning module 110 may be a pen-type optical device. For example, a user can put the optical device directly on an object to be observed or the surrounding of the object and the scanning module 110 can measure the inside of the object at a preset distance from the surface of the object.

In an embodiment, the scanning module 110 may be an endoscopic endomicroscope that is used at hospitals. For example, a medical technician can put the scanning module 110 on the surface of the skin of a patient and the scanning module 110 can measure the state of superficial cells at a depth of 50 um from the contact surface.

Alternatively, for example, a medical technician can put the scanning module 110 on the skin with a portion of a body of a patient open to diagnose cancer or determine the part to be operated, and the scanning module 110 can measure in real time the internal biological tissues at a depth of 70 um from the contact surface.

In this case, a fluorescent dye may have been injected in advance in an injection type, etc. to effectively identify the pathologic state of the internal biological tissues. In this case, the scanning module 110 can emit light to the object and the optical module 120 to be described below can detect a fluorescence signal returning from the object.

Meanwhile, the scanning module 110 can perform scanning in accordance with a driving signal that is applied from the controller 130 to be described below.

The controller 130 may be a component for controlling general scanning of the scanning module 110 described above such that the scanning module 110 performs scanning in accordance with a preset scanning pattern.

The controller 130 can apply a preset driving signal to the scanning module 110. The preset driving signal may include a frequency, a voltage, a phase, etc.

For example, the controller 130 can adjust the frequency, voltage, phase, etc. to change the emission range of light by the scanning module 110.

Alternatively, the controller 130 can control the scanning module 110 to perform scanning based on a driving signal that is input from a user.

The preset scanning pattern may be various and the controller 130 can apply a driving signal corresponding to the preset scanning pattern to the scanning module 110.

In the present disclosure, the controller 130 may include at least one processor.

The optical module 120 is an optical system that applies light to the scanning module 110 and detects a signal returning through the scanning module 110.

In an embodiment of the present disclosure, the optical module 120 may be a confocal endomicroscope system and may be provided as a separate device separately from the scanning module 110 described above.

The optical module 120 may include at least a light emitter 121 and a light receiver 123.

The light emitter 121 may be a laser device that discharges a laser signal of a preset wavelength band. The laser device may be selected in accordance with what image of a reflected image, a fluorescence image, and a transmitted image of an object is to be observed.

For example, in an embodiment of the present disclosure, the laser device may discharge a laser signal of a near infrared range.

For example, for a fluorescence image, the laser signal may use wavelengths of 405 nm, 488 nm, 785 nm, etc., depending on the fluorescent dye to be used. The fluorescent dye can be used to discriminate the pathologic features of internal biological cells, blood vessels, tissues, etc., and ICG, FNa, 5-ALA, and other dyes approved under medical laws may be applied.

As another example, the following Table 1 may be referred to for staining parts of a fluorescent dye and the wavelength band of a laser signal to which the fluorescent dye reacts that may be considered in the present disclosure. The following Table 1 is an example and the present disclosure is not limited thereto.

TABLE 1

| Wavelength band staining part | 400-410 nm | 480-500 nm | 770-800 nm |
|---|---|---|---|
| Nucleus | DAPI (Em: 460 nm, 400-600 nm) | Acriflavine (Em: 515 nm, water) | |
| Nucleus | Hoechst 34580(Em: 450 nm, 400-600 nm) | Acridine orange (Em: 525 nm, 500-650 nm) | |
| Nucleus | Hoechst 33258(Em: 450 nm, 400-600 nm) | Propidium iodide (Em: 620 nm, 580-720 nm) | |
| Other cell parts (cytoplasm) excluding nucleus | 5-ALA | Fluorescein Sodium (FNa) (Em: 505-585 nm) | ICG (Em: 845 nm, 760-880 nm) |
| Other cell parts (cytoplasm) excluding nucleus | | FITC-dextran(Em: 525 nm, 500-630 nm) | |

Referring to Table 1, for example, it is possible to stain a tissue with a fluorescent dye that reacts to a laser signal of a first wavelength band and a fluorescent dye that reacts to a laser signal of a second wavelength band and it is possible to emit laser signals of the first wavelength band and the second wavelength band to the tissue through a laser device.

As described above, Table 1 can be referred to for conditions for obtaining tissue images in the endomicroscope system of the present disclosure. The conditions for obtaining a tissue image in the endomicroscope system of the present disclosure may include staining information of a tissue. The staining information may include whether cells or cytoplasm in a tissue has been stained or the information on a fluorescent dye staining a tissue. Further, the information on a fluorescent dye may include information on at least one of PpIX (5-ALA), Hoechst, DAPI, Acridine orange (AO), Fluorescein Sodium (FNa), Fluorescein isothiocyanate (FITC), Propidium iodide, acriflavine, Indocyanine Green (ICG), Pafolacianine, and Methylene Blue (MB).

Alternatively, the conditions for obtaining a tissue image may include laser information used to obtain a tissue image (operation information of a laser output module of an endomicroscope system). The laser information may include information on first light having a first wavelength or second light having a second wavelength. For example, the first wavelength may be included in one wavelength band of 400 to 410 nm, 480 to 500 nm, and 770 to 800 nm in Table 1 and the second wavelength may be included in a wavelength band different from the wavelength including the first wavelength of 400 to 410 nm, 480 to 500 nm, and 770 to 800 nm in Table 1.

Further, the light emitter 121 can apply an appropriate laser source to the scanning module 110 based on a signal that is input from an optical module control device (not shown).

The optical module control device can control the power of a laser signal that is emitted from the light emitter 121, the gain of an image, etc.

For example, when the endomicroscope system according to an embodiment of the present disclosure is a medical optical device, the power of a laser signal may be set to be emitted at 1 mW or less.

Further, the optical module control device may be provided as a part of the controller 130 described above. In this case, the controller 130 can control the power of a laser signal that is emitted from the light emitter 121, the gain of an image, etc.

The light receiver 123 may be a component for detecting a signal returning from the object by the light emitted through the scanning module 110 from the light emitter 121 described above.

Meanwhile, the light emitter 121 and the light receiver 123 of the present disclosure may be implemented as a single unit in the optical module 120. That is, both of the functions of emitting light and receiving a signal reflected from an object may be implemented through one optical module 120.

Selectively, the endomicroscope system may further include an input unit 140.

For example, the input unit 140 may be an input unit for selecting operation modes of the endomicroscope system. For example, the operation modes may include at least a first mode and a second mode that are set in advance. The first mode may be a low resolution mode or a search mode. Alternatively, the second mode may be a high resolution mode or a zoom-in mode. Accordingly, a user can identify images of appropriate resolution through a display device 150 by selecting the first mode or the second mode, depending on the purposes of use.

Further, for example, the input unit 140 may be an input unit for selecting a working distance of the scanning module 110. For example, the working distance may include a first distance, a second distance, a third distance, etc. that are set in advance, and an input unit corresponding to a preset working distance may be further provided. The working distance may correspond to the focal distance of the lens module to be described below. For example, the controller 130 can perform scanning of the scanning module 110 and calibrating images generated by the scanning module 110 in accordance with a selected working distance.

Meanwhile, in addition to the components described above, input units corresponding to various functions for controlling the operation of the endomicroscope system may be further provided.

Figure 2:
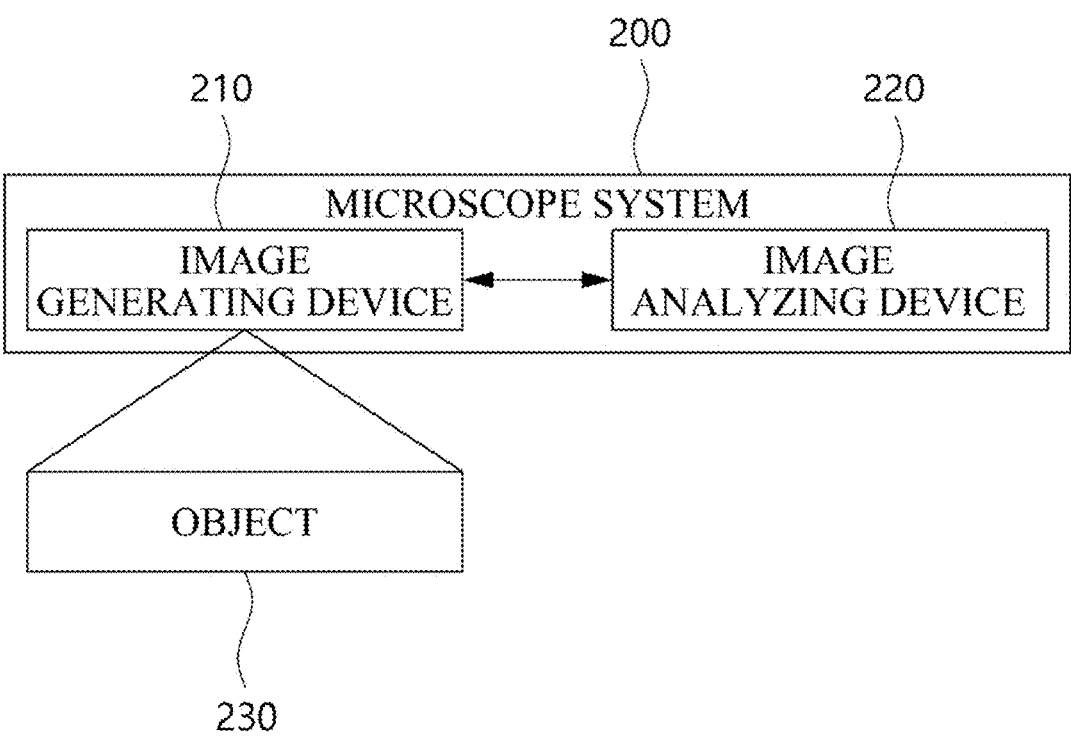
FIG. 2 is a diagram showing an example of an environment in which an endomicroscope system according to an embodiment of the present disclosure is used.

FIG. 2 is a diagram showing an example of an environment in which an endomicroscope system according to an embodiment of the present disclosure is used.

Referring to FIG. 2, an endomicroscope system 200 according to an embodiment of the present disclosure may include an image generating device 210 including at least one of the scanning module 110, the optical module 120, the controller 130, the input unit 140, and the display device 150 described in FIG. 1, and an image analyzing device 220. The endomicroscope system 200 shown in FIG. 2 is an example and the components may be implemented in one device as a module or may be physically separated and positioned at different places. That is, an endomicroscope system not only may mean an endomicroscope itself, but also may mean the entire of an infrastructure for examining an object using components.

The image generating device 210 according to an embodiment of the present disclosure can generate images in real time by scanning an object 230.

For example, the image generating device 210 may be an ultra-small optical fiber scanner for observing the pathologic state of biological tissues in real time at laboratories or operating rooms.

Further, the image analyzing device 220 may be a device for performing pathologic diagnosis in real time using images generated by the image generating device 210.

For example, the image analyzing device 220 may be an electronic device that medical technicians who can perform pathologic diagnosis use. Alternatively, for example, the image analyzing device 220 may be provided in a module type in an electronic device that medical technicians who can perform pathologic diagnosis use. Alternatively, for example, the image analyzing device 220 may be a server that obtains and analyzes images.

Further, the image generating device 210 and the image analyzing device 220 may be connected to each other through a network.

The network may include various wire or wireless networks, and the image generating device 210 and the image analyzing device 220 can transmit and receive various items of information through the network.

For example, the image generating device 210 can transmit images generated by the image generating device 210 to the image analyzing device 220 in real time through the network. The image generating device 210 and the image analyzing device may be positioned at different places. For example, the image generating device may be positioned at an operating room or a laboratory in which operations or biopsies are performed, and the image analyzing device may be positioned at a pathologic diagnosis room or examination room. In this case, the operating room and the pathologic diagnosis room may be positioned at different hospitals or places, whereby tele-pathology can be achieved.

Meanwhile, when the image analyzing device 220 is provided in a module type in an electronic device assigned to a medical technician or is provided in a server type, the image analyzing device 220 may be a program, a software application, or the like for performing pathologic diagnosis based on images that are transmitted in real time from the image generating device 210. Alternatively, the image analyzing device 220 may include an AI model for providing medical diagnosis assistance information that can be referred to for pathologic diagnosis. Alternatively, the image analyzing device 220 may include a pseudo-coloring AI model for converting images generated by the image generating device 210 into images (which may be referred to as virtual H&E images or H&E-like images) having a staining type similar to an H&E image.

For example, a medical technician can make pathologic diagnosis such as cancer diagnosis and operation part determination based on a tissue image displayed on the electronic device.

Further, for example, a medical technician can input information related to cancer diagnosis, operation part determination, etc. through an application that is executed on the electronic device.

Alternatively, for example, the image analyzing device 220 can generate medical diagnosis assistance information for cancer diagnosis, operation part determination, etc. based on a pre-stored image analysis program or AI model.

Alternatively, the image analyzing device 220 can perform pseudo coloring for converting images generated by the image generating device 210 into images having a staining type similar to an H&E image based on a pre-stored image analysis program or AI model.

Further, for example, the image analyzing device 220 can generate medical diagnosis assistance information for cancer diagnosis or operation part determination based on images received from the image generating device 210 and can transmit the medical diagnosis assistance information to the image generating device 210 or another electronic device (not shown).

Alternatively, for example, the image analyzing device 220 can perform pseudo coloring for converting images generated by the image generating device 210 into images having a staining type similar to an H&E image and can transmit pseudo-coloring resultant images to the image generating device 210 or another electronic device (not shown).

Meanwhile, the embodiment described above, to help understanding, exemplifies an environment in which the endomicroscope system 200 including the image generating device 210 and the image analyzing device 220 is used, but the range of the right of the present disclosure is not limited to the example.

Medical technicians can perform pathologic diagnosis based on tissue images obtained through an endomicroscope system.

Even though endomicroscope systems for digital biopsy have been introduced, it takes medical technicians long time to make pathologic diagnoses by observing a large number of tissue images one by one and there is a possibility of wrong diagnoses due to incomplete judgment by medical technicians. Further, actual medical facilities may have limitation, for example, medical facilities may not be equipped with pathologic infrastructures or may not have a department of pathology to which medical technicians who perform pathologic diagnoses pertain, or it is difficult to perform pathologic diagnosis and share the results in the hours excluding the hours for pathology.

If an AI model can analyze tissue images and can generate medical diagnosis assistance information such as cancer diagnosis from the tissue images instead of medical technicians by introducing the AI technology, it would be possible to minimize diagnosis errors by medical technicians.

Accordingly, the present disclosure provides a method of providing medical diagnosis assistance information, which medical technicians may refer to when performing pathologic diagnosis, using the AI technology.

Figure 3:
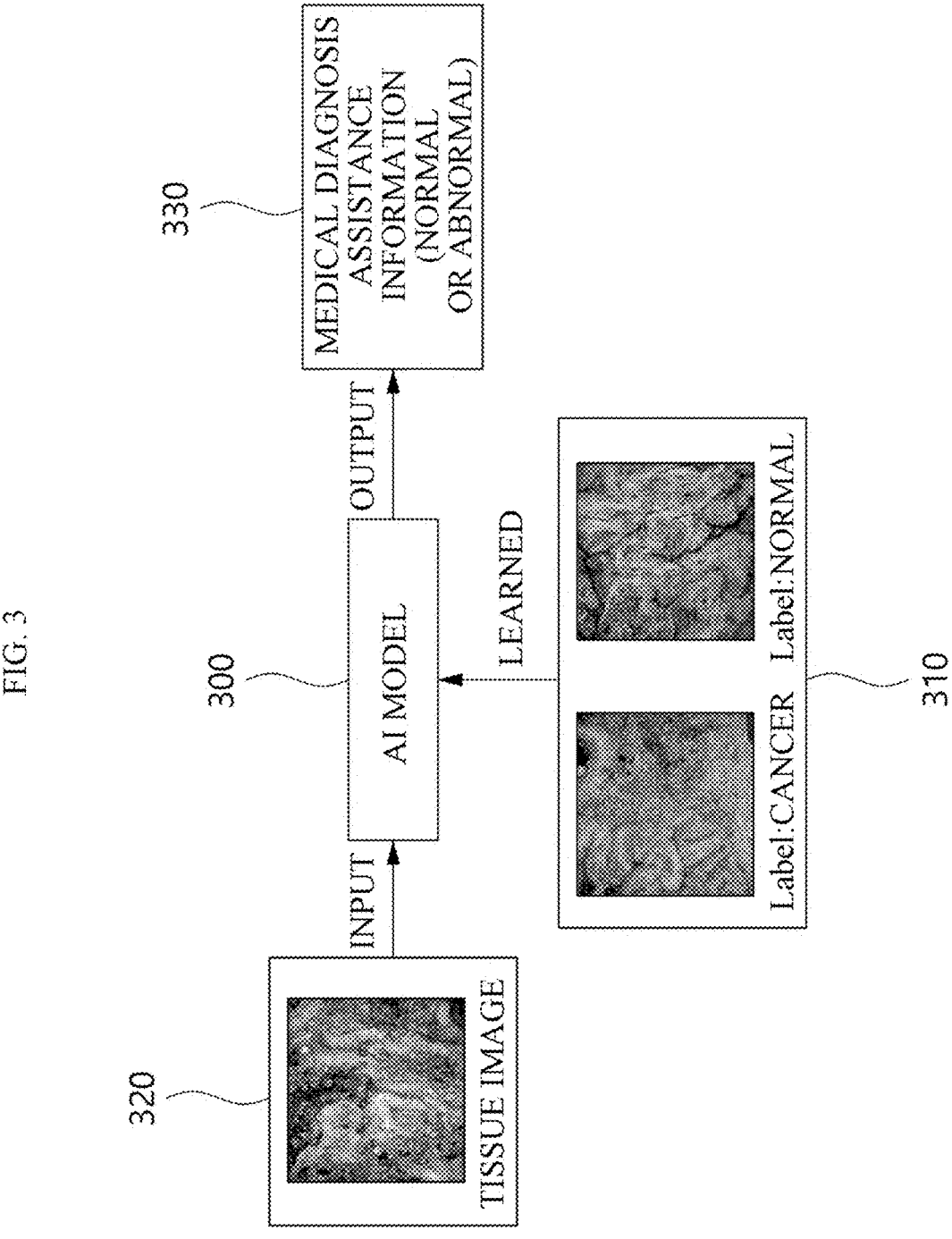
FIG. 3 is a diagram showing a method of providing medical diagnosis assistance information according to an embodiment of the present disclosure.

FIG. 3 is a diagram showing a method of providing medical diagnosis assistance information according to an embodiment of the present disclosure.

Referring to FIG. 3, an AI model 300 may learn a first tissue image 310. The first tissue image 310, which is an image obtained on the basis of at least a portion of a body, for example, may be an image of cells or a tissue taken from a specific part of a body and may be labeled with an indicator showing whether the cells or the tissue is normal or abnormal (e.g., cancer). That is, the first tissue image 310 may include a training image for training the AI model 300. For example, the first tissue image 310 may include an image sliced into a patch of a specific size (e.g., 150 to 200 px) from an entire pathology slide image using H&E staining. The first tissue image 310 may be an image obtained directly from the endomicroscope system or an image obtained from another electronic device or medical device and stored in advance. Meanwhile, the first tissue image 310 that is used for training the AI model 300 may be obtained through various methods and the present disclosure is not limited thereto. Further, the AI model 300 may be implemented by a convolution neural network (CNN) algorithm including Inception or Xception. Meanwhile, the present disclosure is not limited thereto and the AI model 300 may be implemented by various algorithms.

The AI model 300 that learned the first tissue image 310 may receive a second tissue image 320 to be observed by a medical technician. The second tissue image 320 may be an image obtained from the endomicroscope system described above or an image selected from pre-stored images by a medical technician. Meanwhile, tissue images that are input to an AI model may be obtained through various methods and the present disclosure is not limited thereto.

The AI model 300 may output medical diagnosis assistance information 330 about the second tissue image 320. For example, the AI model 300 may output information, which shows whether the tissue related to the second tissue image 320 is normal or abnormal (e.g., cancer), as medical diagnosis assistance information 330. Alternatively, for example, the AI model 300 may output the probability that the tissue related to the second tissue image 320 is abnormal (e.g., cancer) or normal, as medical diagnosis assistance information 330. Further, the AI model 300 may generate and output a new image (e.g., a third tissue image) showing the medical diagnosis assistance information 330 in the received second tissue image 320. The medical diagnosis assistance information 330 may be displayed on the display device of an endomicroscope system or an external device.

A medical technician may be provided with the medical diagnosis assistance information 330 output from the AI model 300 and may perform pathologic diagnosis with reference to the medical diagnosis assistance information 330.

The performance of the AI model 300 shown in FIG. 3, that is, the accuracy of the medical diagnosis assistance information 330 may be determined usually by a learning dataset, a validation dataset, and a test dataset, and various algorithms (network), hyper parameter (e.g., a learning rate, the size of hidden layers, the number of hidden layers, etc.) tuning, and data preprocessing may be performed to improve the accuracy. That is, the performance of the AI model 300 that generates medical diagnosis assistance information may depend on the accuracy of the algorithm that implements the AI model 300. The algorithm that implements the AI model 300 outputs results with relatively high accuracy, but some results may include errors. In particular, there may be a problem that even though a tissue is substantially abnormal (e.g., cancer), the AI model 300 generates and outputs information showing that the tissue is normal. In this case, it is required to explain the process or the basis causing this result in addition to the fact that the AI model 300 generates medical diagnosis assistance information as a result in accordance with the algorithm. In order to provide medical technicians with more accurate and reliable medical diagnosis assistance information in the medical environment in which small mistakes cause fatal results, it is required to visualize and additionally provide information explaining the basis that the AI model 300 generates medical diagnosis assistance information to medical technicians, for example, through visualization or it is required to provide a medical technicians with effective medical diagnosis assistance information that can be used for pathologic diagnosis except for unnecessary information.

Meanwhile, the AI model 300 may show the region that is the basis of determining whether the cells or the tissue in the second tissue image 320 is cancer or normal. For example, the AI model 300 may create an activation map (or a heat map) showing the region that is the basis of determining whether the cells or the tissue in the second tissue image 320 is cancer or normal. Alternatively, the generated image (third tissue image) may include an activation map created based on the second tissue image. The activation map may be a map visually showing the region, which was used a lot by the AI model 330 to generate the medical diagnosis assistance information 330 in the entire region of the second tissue image, in the second tissue image. The AI model 300 may create an activation map through class activation mapping (CAM). Meanwhile, in the present disclosure, the region used by an AI model to generate medical diagnosis assistance information in the entire region of a tissue image may be referred to as an activated region.

Figure 4A:
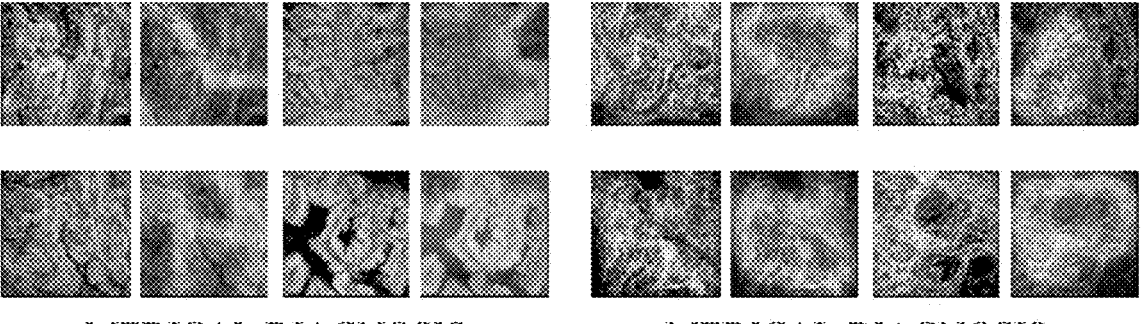
FIG. 4A and FIG. 4B are diagrams showing an example of activation maps created by an AI model according to an embodiment of the present disclosure.
Figure 4B:
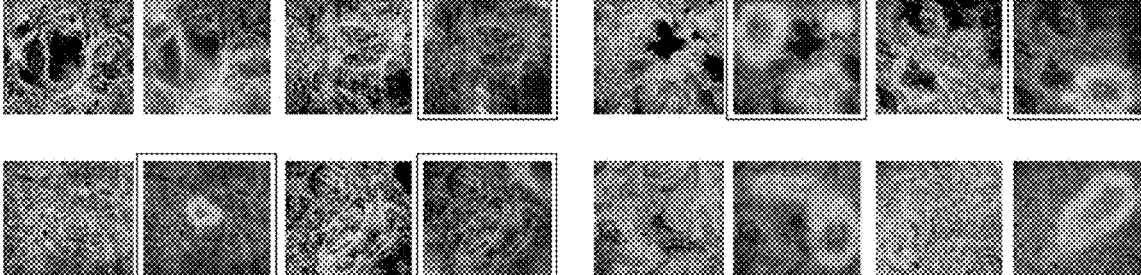

FIG. 4A and FIG. 4B are diagrams showing an example of activation maps created by an AI model according to an embodiment of the present disclosure.

FIG. 4A shows activation maps showing activated regions considered when an AI model generates medical diagnosis assistance information in the entire regions of tissue images.

Referring to FIG. 4A, when medical diagnosis assistance information generated by the AI model coincides with an actual pathologic diagnosis by a medical technician, the activated region considered when the medical diagnosis assistance information is generated is continuous and shown throughout the entire area in an activation map. In this case, the activated region considered when the AI model generates medical diagnosis assistance information may be considered as being similar to the region that the medical technician observes when making a pathologic diagnosis in the entire region of the tissue image. Accordingly, the medical diagnosis assistance information when an activated region is continuous and shown throughout the entire area may be determined as effective information that can be used for actual pathologic diagnosis.

FIG. 4B shows activation maps showing activated regions considered when an AI model generates medical diagnosis assistance information in the entire region of tissue images.

Referring to FIG. 4B, when medical diagnosis assistance information generated by the AI model does not coincide with an actual pathologic diagnosis by a medical technician, the activated region considered when the medical diagnosis assistance information is generated is locally and peripherally shown in an activation map. Meanwhile, actually, medical technicians do not perform pathologic diagnosis, for example, that cells or a tissue is cancer or normal by seeing only local regions of a tissue image. Accordingly, medical diagnosis assistance information when an activated region is locally and peripherally shown may be determined as ineffective information that is not used for actual pathologic diagnosis.

When ineffective medical diagnosis assistance information is provided to a medical technician, it may cause incomplete judgment of the medical technician. Accordingly, the present disclosure provides a method of providing medical diagnosis assistance information based on distribution of an activated region in an activation map.

Figure 5:
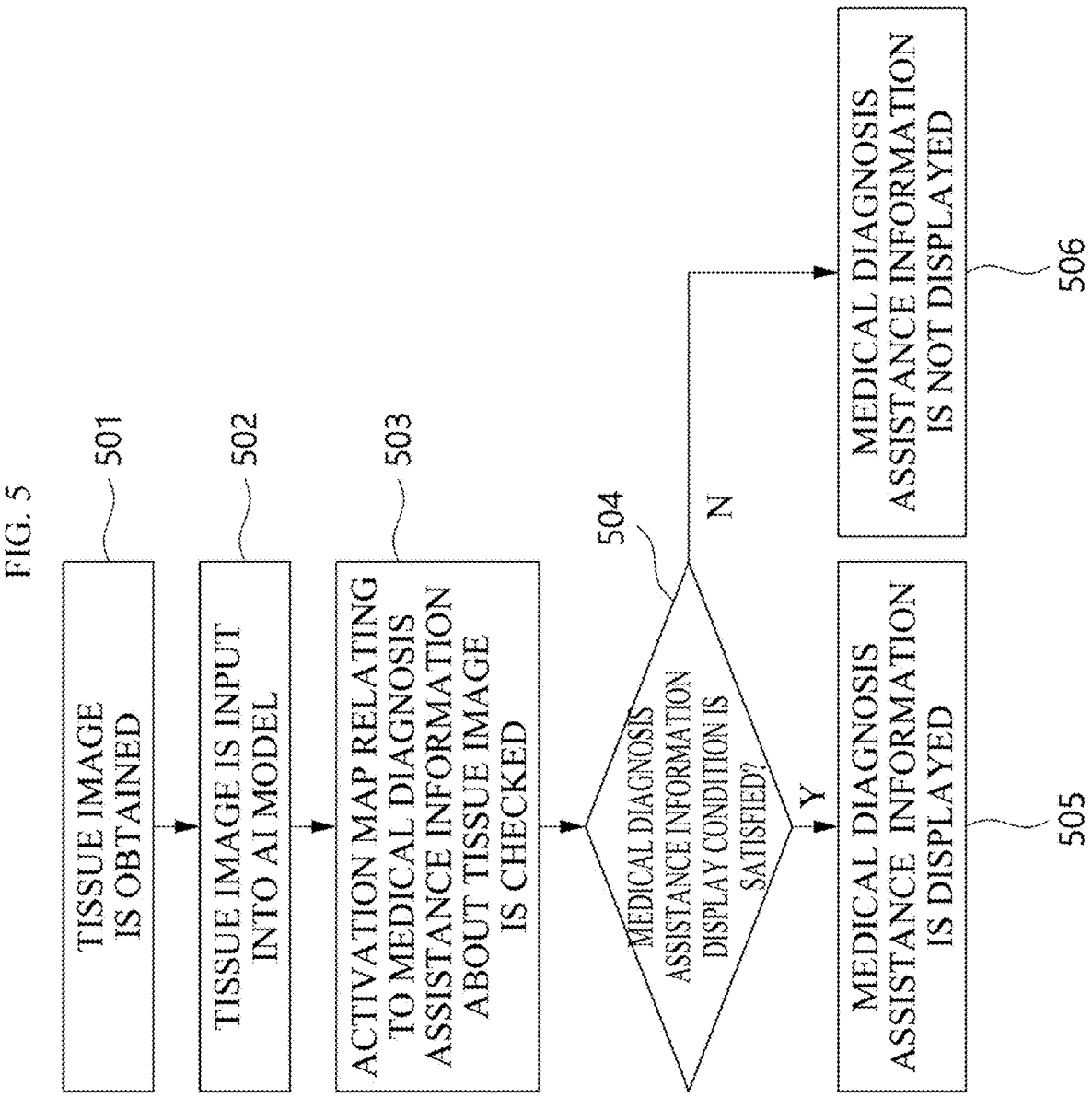
FIG. 5 is a diagram showing a method of providing medical diagnosis assistance information based on distribution of an activated region in an activation map according to an embodiment of the present disclosure.

FIG. 5 is a diagram showing a method of providing medical diagnosis assistance information based on distribution of an activated region in an activation map according to an embodiment of the present disclosure.

Each step of a method of producing and displaying medical diagnosis assistance information may be performed by various types of electronic device, such as the endomicroscope system described above. Hereafter, a method of providing medical diagnosis assistance information by the controller 130 of the endomicroscope system of the present disclosure is mainly described.

In step 501, the endomicroscope system may obtain a tissue image of cells or a tissue. For example, the endomicroscope system may generate a first driving signal corresponding to a first axis and a second driving signal corresponding to a second axis different from the first axis. The endomicroscope system may control a light receiver to detect excitation light generated by light emitted from an end of a laser scanner operating on the basis of the first driving signal and the second driving signal. Thereafter, the endomicroscope system may generate a tissue image of a tissue on the basis of the detected excitation light. Alternatively, the endomicroscope system may receive selection of a tissue image by a user (e.g., medical technician) and may identify the selected tissue image in a plurality of pre-stored images.

In step 502, the endomicroscope system may input the obtained tissue image into an AI model.

Meanwhile, the tissue image that the AI model producing medical diagnosis assistance information received may not include features that can make a diagnosis of normality or abnormality (e.g., cancer). Further, when a tissue image is obtained through the endomicroscope system of the present disclosure, a tissue image from which it is difficult to derive a diagnosis result may be obtained because the tissue was photographed in a non-refined environment. For example, there may be a case in which it is impossible to derive a diagnosis result of normality/abnormality for a tissue image due to various artifacts (e.g., a movement artifact, out-of-focus, insufficient intensity of a fluorescence signal, or dirt on a lens) generated when the tissue image is obtained. When a sorted tissue image is input into an AI model, the AI model would be able to generate more accurate medical diagnosis assistance information.

In an embodiment of the present disclosure, it is possible to exclude an image having high possibility of producing low-accuracy medical diagnosis assistance information (e.g., a blurred image due to movement, out-of-focus, or the like) from a tissue image set that is input to an AI model.

To this end, the endomicroscope system may identify whether it is possible to generate medical diagnosis assistance information for the tissue image obtained in step 501 before performing step 502. Alternatively, the endomicroscope system may identify whether it is possible to make a diagnosis of normality of abnormality about the tissue image obtained in step 501 before performing step 502. Alternatively, the endomicroscope system may identify whether the tissue image obtained in step S501 satisfies a medical diagnosis assistance information condition before performing step 502. For example, when the tissue image obtained in step 501 is a blurred image due to a movement artifact, out-of-focus, or the like, the endomicroscope system may determine that it is impossible to generate medical diagnosis assistance information on the tissue image, it is impossible to make a diagnosis of normality or abnormality about the tissue image, or the tissue image does not satisfy a medical diagnosis assistance information condition. In this case, the endomicroscope system may return to step 501 and obtain a tissue image. Alternatively, the endomicroscope system may display information showing that re-photographing is required to obtain a new tissue image or information of holding production of medical diagnosis assistance information on the display device or can transmit the information to an external device such that the external device display the information.

In step 503, the endomicroscope system may identify medical diagnosis assistance information on the tissue image output from the AI model or an activation map related to the medical diagnosis assistance information.

In step 504, the endomicroscope system may identify whether the activation map related to the medical diagnosis assistance information satisfies a display condition of the medical diagnosis assistance information. For example, the endomicroscope system may identify whether at least one of the size of an activated region in an activation map and the number of closed loops in an activation map satisfies a predetermined condition.

In step 505, when the activation map satisfies the display condition of medical diagnosis assistance information, the endomicroscope system of the present disclosure may decide to provide medical diagnosis assistance information on the tissue image. For example, the endomicroscope system may display the medical diagnosis assistance information about the tissue image on the display device or transmit the medical diagnosis assistance information to an external device such that the external device displays the medical diagnosis assistance information. Accordingly, a medical technician may make a pathologic diagnosis on the cells or the tissues with reference to the provided medical diagnosis assistance information.

In step 506, when the activation map does not satisfy the display condition of medical diagnosis assistance information, the endomicroscope system may decide not to provide medical diagnosis assistance information on the tissue image. For example, the endomicroscope system may discard the medical diagnosis assistance information on the tissue image without displaying the medical diagnosis assistance information. Alternatively, the endomicroscope system may display a message saying that new medical diagnosis assistance information is required about the tissue image or may transmit the message to an external device such that the external device displays the message. Accordingly, a medical technician is able to hold or not to perform pathologic diagnosis about the cells or the tissue related to the tissue image.

When it is possible to determine whether to display medical diagnosis assistance information based on an activation map related to the medical diagnosis assistance information on a tissue image in accordance with the method described in FIG. 5, medical technicians may be provided with effective medical diagnosis assistance information that they may refer to for actual pathologic diagnosis. Accordingly, medical technicians may more accurately and quickly perform pathologic diagnosis.

Hereafter, step 504 of identifying whether display conditions of medical diagnosis assistance information are satisfied through an activation map of the medical diagnosis assistance information is described in detail with reference to FIG. 6A and FIG. 6B.

FIG. 6A and FIG. 6B are diagrams showing an example of display conditions of medical diagnosis assistance information according to an embodiment of the present disclosure.

FIG. 6A shows an example of considering the ratio between the entire region and an activated region in an activation map.

Referring to FIG. 6A, whether a medical diagnosis assistance information display condition is satisfied may be identified on the basis of the ratio between the entire region and an activated region in an activation map. When the size of an activated region at a specific color threshold is less than a specific ratio to the entire region in an activation map, it is possible to determine that a medical diagnosis assistance information display condition is not satisfied. Alternatively, when the size of an activated region at a specific color threshold is a specific ratio or more to the entire region in an activation map related to medical diagnosis assistance information, it is possible to determine that a medical diagnosis assistance information display condition is satisfied. The specific color threshold may be a pre-designated value or a value selected by a user of an endomicroscope system. For example, the specific color threshold may be 150. Further, the specific ratio may be a pre-designated value or a value selected by a user of an endomicroscope system. For example, the specific ratio may be 5%.

FIG. 6B shows an example of considering whether an activated region is continuous in an activation map.

Referring to FIG. 6B, whether a medical diagnosis assistance information display condition is satisfied may be identified based on whether an activated region is continuous or discontinuous in an activation map. When an activated region at a specific color threshold is dispersed in an activation map, it is possible to determine that a medical diagnosis assistance information display condition is not satisfied. Alternatively, when an activated region at a specific color threshold is continuous in an activation map, it is possible to determine that a medical diagnosis assistance information display condition is satisfied. The fact that an activated region is dispersed may mean that the number of closed loops of the activated region in the activation map is a predetermined number or more. Further, the fact that an activated region is continuous may mean that the number of closed loops of the activated region in the activation map is less than a predetermined number. The predetermined number may be 2.

Alternatively, at least one of the size of an activated region in an activation map and whether an activation region is continuous may be considered as a medical diagnosis assistance information display condition. For example, when the size of an activated region at a specific color threshold is less than a specific ratio to the entire region in an activation map or when the activated region is dispersed, it is possible to determine that a medical diagnosis assistance information display condition is not satisfied. Alternatively, when the size of an activated region at a specific color threshold is a specific ratio or more to the entire region in an activation map and the activated region is continuous, it is possible to determine that a medical diagnosis assistance information display condition is satisfied.

Meanwhile, an endomicroscope system to which an embodiment of the present disclosure can be applied may obtain a tissue image based on excitation light generated by emitting light (lasers) having different bands. For example, referring to Table 1 described above, a tissue to be observed through an endomicroscope system may be stained with a fluorescent dye that reacts to light having a first wavelength band (e.g., one of 400 to 410 nm, 480 to 500 nm, and 770 to 800 nm) or a fluorescent dye that reacts to light having a second wavelength band different from the first wavelength band. An endomicroscope system of the present disclosure may obtain a plurality of tissue images of same cells or a same tissue through a method of obtaining a first tissue image by emitting light having the first wavelength band, obtaining a second tissue image by emitting light having the second wavelength band, or obtaining a third tissue image by emitting both of the light having the first wavelength band and the light having the second wavelength band. By using such a plurality of tissue image, it may be possible to generate more reliable medical diagnosis assistance information in comparison to the case of considering a single tissue image. Accordingly, the present disclosure provides a method of producing medical diagnosis assistance information using a plurality of tissue images obtained for the same cells or the same tissue. This is described with reference to FIG. 7A and FIG. 7B.

Figure 7A:
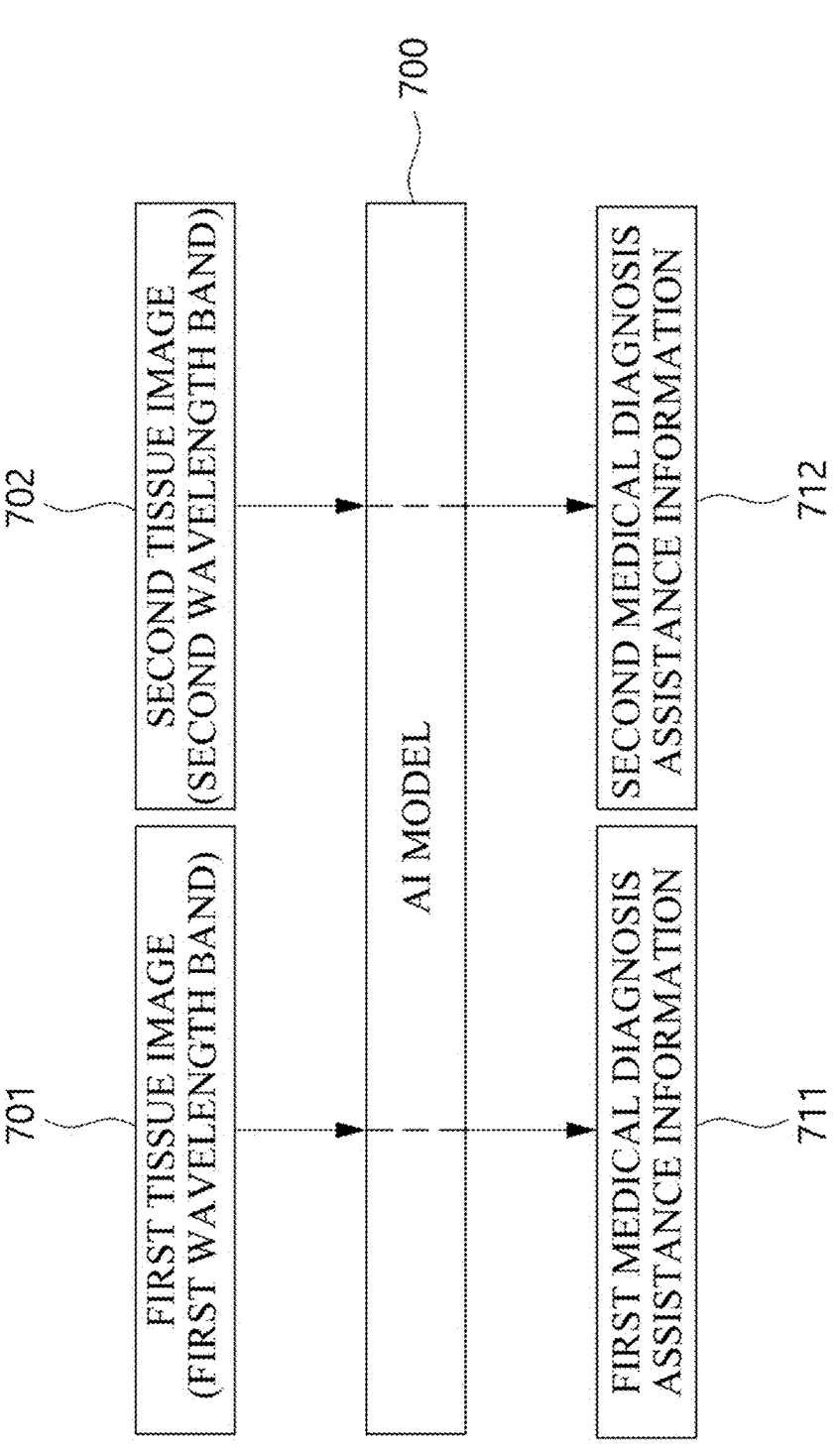
FIG. 7A and FIG. 7B are diagrams showing a method of providing medical diagnosis assistance information using a plurality of tissue images according to an embodiment of the present disclosure.
Figure 7B:
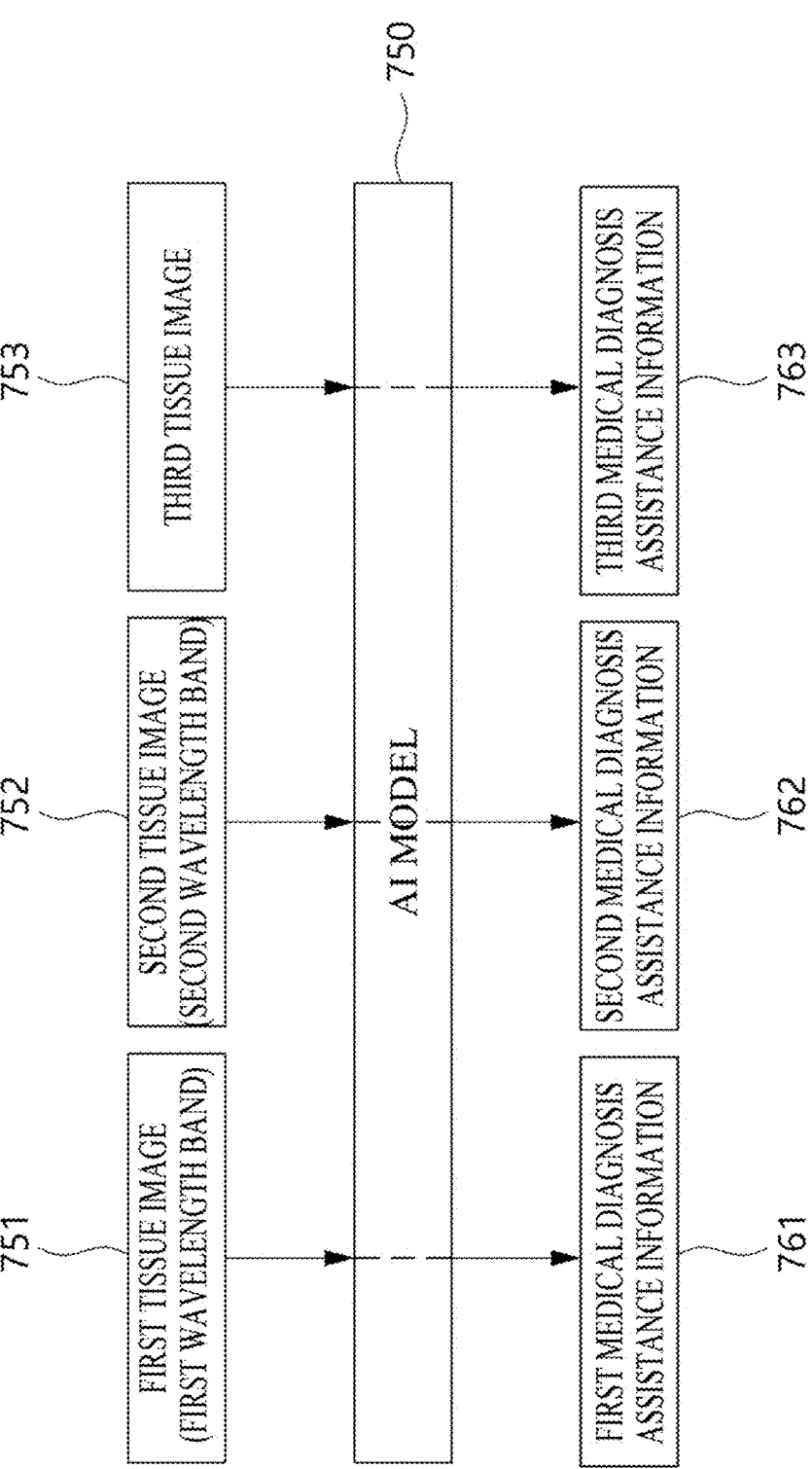

FIGS. 7A and 7B are diagrams showing a method of providing medical diagnosis assistance information using a plurality of tissue images according to an embodiment of the present disclosure.

Referring to FIG. 7A, a first tissue image 701 obtained by emitting light having a first wavelength band and a second tissue image 702 obtained by emitting light having a second wavelength band different from the first wavelength band may be input to an AI model 700. According to the embodiment described above, the AI model 700 may output first medical diagnosis assistance information 711 about the first tissue image 701 and second medical diagnosis assistance information 712 about the second tissue image 702. Whether a display condition is satisfied may be identified for each item of medical diagnosis assistance information in accordance with the embodiment described above, and accordingly, corresponding medical diagnosis assistance information may be displayed or may not be displayed. A medical technician may make a more accurate pathologic diagnosis with reference to the displayed first medical diagnosis assistance information 711 and second medical diagnosis assistance information 712.

Meanwhile, an endomicroscope system of the present disclosure may generate and display third medical diagnosis assistance information based on the first medical diagnosis assistance information 711 and the second medical diagnosis assistance information 712. For example, it is possible to set a specific weight for each item of medical diagnosis assistance information and generate third medical diagnosis assistance information by performing weight calculation on the first medical diagnosis assistance information 711 and the second medical diagnosis assistance information 712. The specific weight may be a value set in advance for each wavelength band or a value input from the user of the endomicroscope system.

Alternatively, the endomicroscope system of the present disclosure may select and display one that satisfies a specific condition from the first medical diagnosis assistance information 711 and the second medical diagnosis assistance information 712. For example, the endomicroscope system may select and display medical diagnosis assistance information that satisfies the medical diagnosis assistance information condition described in FIGS. 5 to 6B from the first medical diagnosis assistance information 711 and the second medical diagnosis assistance information 712. Alternatively, the endomicroscope system may select and display medical diagnosis assistance information, in which the number of closed loop of an activated region is the smallest, from the first medical diagnosis assistance information 761 and the second medical diagnosis assistance information 762.

Referring to FIG. 7B, a first tissue image 751 obtained by emitting light having a first wavelength band, a second tissue image 752 obtained by emitting light having a second wavelength band different from the first wavelength band, and a third tissue image 753 may be input to an AI model 750. The third tissue image 753 may be an image generated based on the first tissue image 751 and the second tissue image 752. For example, the third tissue image 753 may be a combination image of the first tissue image 751 and the second tissue image 752. Alternatively, the third tissue image 753 may be an image obtained by emitting multi-wavelength light having both of the first wavelength band and the second wavelength band. In this case, the tissue to which light has been emitted may be a tissue stained with both of a fluorescent dye that reacts to the first wavelength band and a fluorescent dye that reacts to the second wavelength band.

According to the embodiment described above, the AI model 750 may output first medical diagnosis assistance information 761 about the first tissue image 751, second medical diagnosis assistance information 762 about the second tissue image 752, and third medical diagnosis assistance information 763 about the third tissue image 753. Whether a display condition is satisfied may be identified for each item of medical diagnosis assistance information in accordance with the embodiment described above, and accordingly, corresponding medical diagnosis assistance information may be displayed or may not be displayed. A medical technician may make a more accurate pathologic diagnosis with reference to the displayed first medical diagnosis assistance information 761, second medical diagnosis assistance information 762, and third medical diagnosis assistance information 763.

Meanwhile, an endomicroscope system of the present disclosure may generate and display fourth medical diagnosis assistance information based on the first medical diagnosis assistance information 761, the second medical diagnosis assistance information 762, and the third medical diagnosis assistance information 763. For example, it is possible to set a specific weight for each item of medical diagnosis assistance information and generate fourth medical diagnosis assistance information by performing weight calculation on the first medical diagnosis assistance information 761, the second medical diagnosis assistance information 762, and the third medical diagnosis assistance information 763. The specific weight may be a value set in advance for each wavelength band or a value input from the user of the endomicroscope system.

Alternatively, the endomicroscope system of the present disclosure may select and display one that satisfies a specific condition from the first medical diagnosis assistance information 761, the second medical diagnosis assistance information 762, and the third medical diagnosis assistance information 763. For example, the endomicroscope system may select and display medical diagnosis assistance information that satisfies the medical diagnosis assistance information condition described in FIGS. 5 to 6B from the first medical diagnosis assistance information 761, the second medical diagnosis assistance information 762, and the third medical diagnosis assistance information 763. Alternatively, the endomicroscope system may select and display medical diagnosis assistance information, in which the number of closed loop of an activated region is the smallest, from the first medical diagnosis assistance information 761, the second medical diagnosis assistance information 762, and the third medical diagnosis assistance information 763.

When tissue images are obtained through an endomicroscope system of the present disclosure, the properties (e.g., brightness, noise, etc.) of the images may be different for each part of a body. Accordingly, the present disclosure provides a method of providing medical diagnosis assistance information by setting the number of specific images for each part of a body and using a plurality of tissue images by the number of the specific images.

Figure 8:
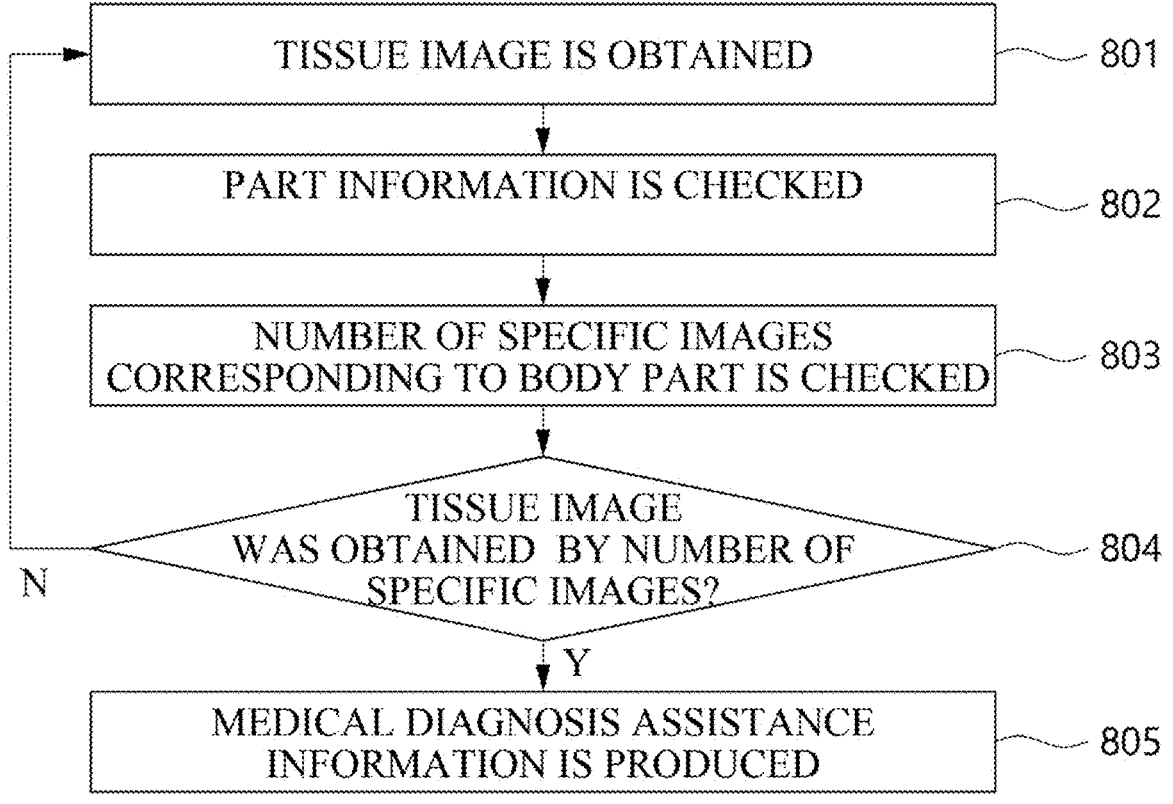
FIG. 8 is a diagram showing a method of providing medical diagnosis assistance information using a plurality of tissue images by the number of specific images for each part of a body according to an embodiment of the present disclosure.

FIG. 8 is a diagram showing a method of providing medical diagnosis assistance information using a plurality of tissue images by the number of specific images for each part of a body according to an embodiment of the present disclosure.

In step 801, an endomicroscope system may obtain a tissue image of cells or a tissue. The method in which an endomicroscope system obtains a tissue image was described above, so it is not described here.

In step 802, the endomicroscope system may identify a body part (e.g., organ information) of the cells or the tissue in the tissue image. The body part may include at least one of a brain, a prostate, or a lung but is not limited thereto. Meanwhile, the step of identifying organ information of step 802 may include a step of receiving information on the body part of the tissue image from a user. Alternatively, the endomicroscope system may identify a body part corresponding to an obtained tissue image based on the tissue image.

In step 803, the endomicroscope system may identify the number of specific images corresponding to the body part. The number of specific images may mean the minimum number of images required to generate medical diagnosis assistance information. For example, the number of specific image for each body part may be as in Table 2

TABLE 2

| Part | Disease name | Number of specific images |
|---|---|---|
| Brain | Brain tumor | N |
| Prostate | Prostatic cancer | M |
| Lung | Lung cancer | K |

In Table 2, the body parts, the disease names, and the numbers of specific images may be set in advance or may be input and set by a user of an endomicroscope system. Further, in Table 2, N, M, and K may be certain natural numbers.

In step 804, the endomicroscope system may identify whether tissue images have been obtained by the number of specific images identified in step 803.

When tissue images have not been obtained by the number of specific images, the endomicroscope system may return to step 801 and obtain a tissue image.

When tissue images have been obtained by the number of specific images, the endomicroscope system may generate and display medical diagnosis assistance information based on a plurality of obtained tissue images in step 805. For example, the endomicroscope system may generate and display medical diagnosis assistance information on each of the obtained tissue images. Whether a display condition is satisfied may be identified for each item of medical diagnosis assistance information in accordance with the embodiment described above, and accordingly, corresponding medical diagnosis assistance information may be displayed or may not be displayed. Alternatively, as described in FIG. 7A and FIG. 7B, the endomicroscope system may generate medical diagnosis assistance information on each of the obtained tissue images and may generate final medical diagnosis assistance information based on the medical diagnosis assistance information on the tissue images.

According to the method described in FIG. 8, since the minimum number of images required to generate medical diagnosis assistance information is secured for each body part, more accurate and reliable medical diagnosis assistance information may be provided.

Meanwhile, in a specific environment (e.g., an ex-vivo environment), it is possible to obtain a tissue image of a portion of a specific body part while moving a probe (or scanner) of an endomicroscope system and obtain an entire tissue image of the specific body part by stitching such tissue images. According to the embodiment described above, an endomicroscope system may obtain a tissue image of a portion of a specific body part and may generate medical diagnosis assistance information (e.g., whether it is normal or abnormal (e.g., cancer)) about the tissue image. In this case, when there is one or more images determined as abnormal (e.g., cancer) even though most images were determined as normal and the distance between the one or more images is large, it may mean that the medical diagnosis assistance information on the one or more images is not accurate. Similarly, when there is one or more images determined as normal even though most images were determined as abnormal (e.g., cancer) and the distance between the one or more images is large, it may mean that the medical diagnosis assistance information on the one or more images is not accurate. Hereafter, this is described in detail with reference to FIG. 9.

FIG. 9 is a diagram showing a method of providing medical diagnosis assistance information in a specific environment according to an embodiment of the present disclosure.

Referring to FIG. 9, it is possible to continuously obtain tissue images corresponding to the size of a field of view (FOV) while moving a probe of an endomicroscope system of the present disclosure along a predetermined pattern in a specific environment (e.g., an ex-vivo environment). It is possible to obtain an entire tissue image of a specific body part by stitching the continuously obtained tissue images along the pattern. The number of the continuously obtained tissue images may be the number of specific images of each body part described in FIG. 8.

In accordance with the embodiment described above, an endomicroscope system may generate medical diagnosis assistance information (e.g., showing normality or abnormality) about each of continuously obtained tissue images.

Thereafter, when the number of one or more tissue images having first type medical diagnosis assistance information (e.g., diagnosis of abnormality (e.g., cancer)) in the continuously obtained images is a predetermined number or less and the number of the one or more tissue images exceeds a predetermined distance 'd', it is possible to ignore the medical diagnosis assistance information on the one or more tissue images. Further, the endomicroscope system may display a message of requesting new medical diagnosis assistance information on the one or more images through a display device or an external device. The predetermined number and the predetermined distance 'd' may be set for each body part.

Thereafter, when the number of one or more tissue images having second type medical diagnosis assistance information (e.g., diagnosis of normality) in the continuously obtained images is a predetermined number or less and the number of the one or more tissue images exceeds a predetermined distance 'd', it is possible to ignore the medical diagnosis assistance information on the one or more tissue images. Further, the endomicroscope system may display a message of requesting new medical diagnosis assistance information on the one or more images through a display device or an external device. The predetermined number and the predetermined distance 'd' may be set for each body part.

According to the method described in FIG. 9, it is possible to collect more accurate medical diagnosis assistance information in relation to an interested body part when continuously obtaining tissue images while moving a probe of the endomicroscope system along a predetermined pattern.

In the embodiment described above, a method in which an AI model that has learned tissue images in advance receives a new tissue image and outputs medical diagnosis assistance information was disclosed. Meanwhile, tissue images that an AI model learns may be obtained in accordance with specific conditions such as the wavelength band of light used by an endomicroscope system and a body part. Accordingly, when an AI model may learn not only a tissue image, but also the condition under which the tissue image was obtained, the AI model would be able to generate more accurate medical diagnosis assistance information. Accordingly, the present disclosure proposes a method of training an AI model in consideration conditions under which tissue images were obtained.

Figure 10:
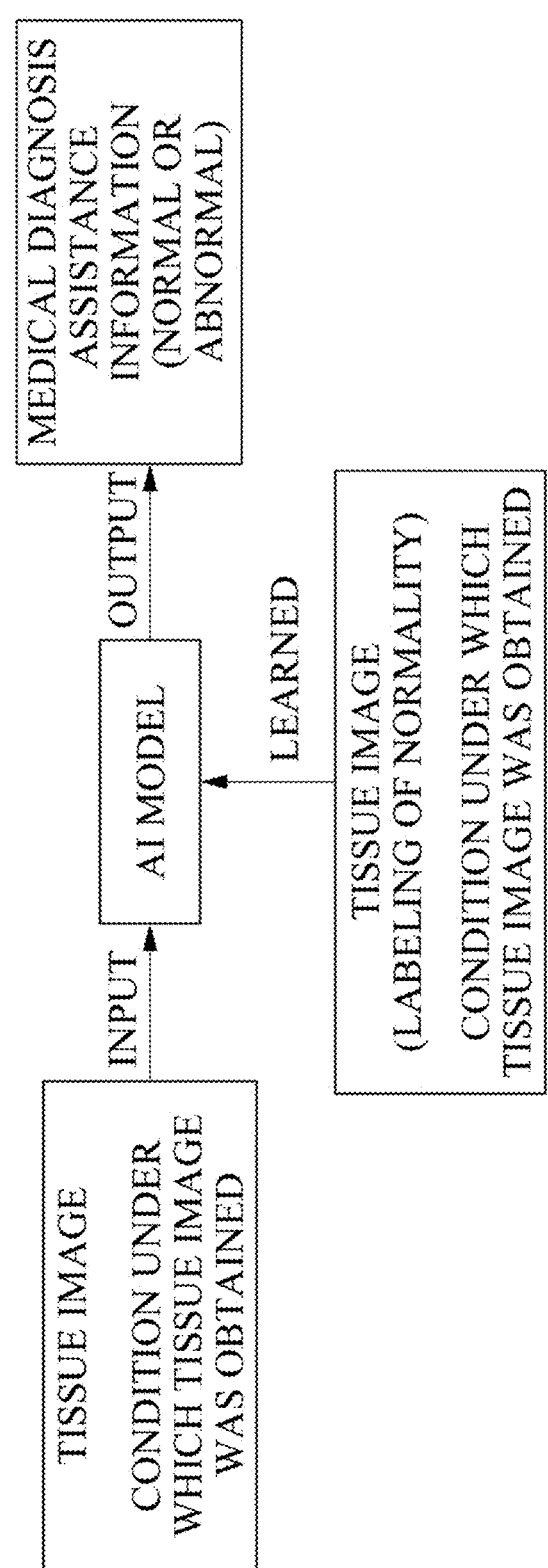
FIG. 10 is a diagram showing an AI model that has learned a condition in which a tissue image was obtained in accordance with an embodiment of the present disclosure.

FIG. 10 is a diagram showing an AI model that has learned a condition in which a tissue image was obtained in accordance with an embodiment of the present disclosure.

Referring to FIG. 10, an AI model may learn a tissue image and a condition (e.g., the wavelength band of light, organ information of cells or a tissue, etc.) under which the tissue image was obtained. The tissue image may be labeled with an indicator showing that the tissue is normal or abnormal (e.g., cancer). The tissue image that the AI model learns may be an image obtained directly from an endomicroscope system or an image obtained from another electronic device or medical device and stored in advance. Meanwhile, tissue images that are used to train the AI model may be obtained through various methods and the present disclosure is not limited thereto. Further, Table 1 described above may be referred to for conditions under which tissue images that the AI model learns were obtained.

The AI model may receive a tissue image and a condition (e.g., the wavelength band of light, organ information of cells or a tissue, etc.) under which the tissue image was obtained. The tissue image that the AI model received may be an image obtained from the endomicroscope system described above or an image selected from pre-stored images by a medical technician. Meanwhile, tissue images that are input to the AI model may be obtained through various methods and the present disclosure is not limited thereto. Further, Table 1 described above may be referred to for conditions under which tissue images that the AI model received were obtained.

The AI model may generate medical diagnosis assistance information on the received tissue image.

Meanwhile, when the endomicroscope system of the present disclosure obtains tissue images, the light source intensity of a laser required for tissues may be different. When an endomicroscope system may emit a laser to cells or a tissue that is an object with optimal light source intensity, it would be possible to obtain high-quality images. Accordingly, the present disclosure proposes a method of determining optimal light source intensity in accordance with cell information or organ information through an AI model.

Figure 11:
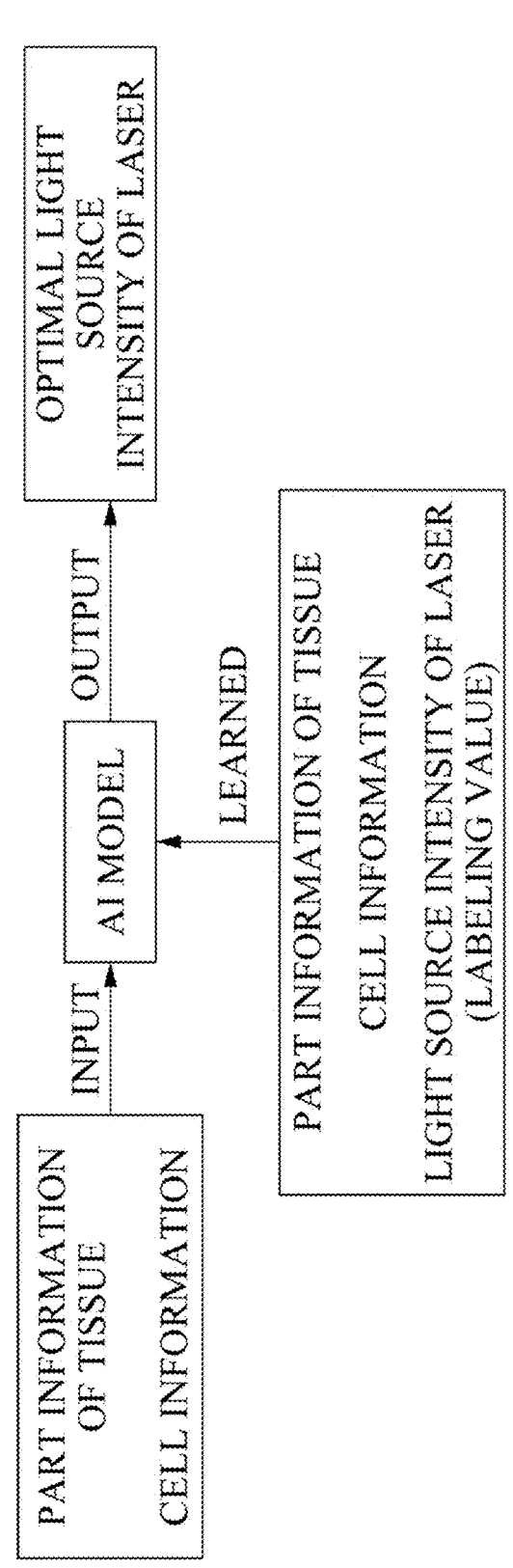
FIG. 11 is a diagram showing an AI model that determines optimal light source intensity of a laser according to an embodiment of the present disclosure.

FIG. 11 is a diagram showing an AI model that determines optimal light source intensity of a laser according to an embodiment of the present disclosure.

Referring to FIG. 11, an AI model may learn organ information of a tissue, cell information (e.g., the number of cell nuclei in a tissue), and the light source intensity of a laser that is a labeling value.

The AI model may receive organ information of a tissue and cell information (e.g., a tissue image or information on the number of cell nuclei in a tissue).

The AI model may output optimal light source intensity of the laser in relation to the received organ information of a tissue and cell information.

Accordingly, an endomicroscope system may obtain a high-quality tissue image by emitting a laser to cells or a tissue at the optimal light source intensity output from the AI model.

Meanwhile, an endomicroscope system for digital biopsy of the present disclosure may not need a pathologic slide that uses H&E staining. Accordingly, the types of tissue images obtained through the endomicroscope system may be different from H&E images familiar to medical technicians. For example, when comparing a tissue image obtained from a pathologic slide using H&E staining and a tissue image obtained through the endomicroscope system of the present disclosure, it is as in the following Table 3. Meanwhile, Table 3 is only an example for the convenience of description and the present disclosure is not limited thereto.

TABLE 3

|  | Tissue image obtained from pathologic slide using H&E staining | Tissue image obtained through endomicroscope system of present disclosure |
|---|---|---|
| Color Matrix | Red/Green/Blue | Grayscale |
| Background color | White | Black |
| Dye | Hematoxylin(nucleus), Eosin(cytoplasm) | Referring to Table 1, for example, AO(nucleus), FNA, ICG(cytoplasm) |
| Object to be photographed | Thin cut-off tissue slide (2D) | Cut-off tissue (3D) |
| FOV | Unit of mm (e.g., 5 mm × 5 mm) | Unit of μm (e.g., 500 μm × 500 μm) |
| Resolution of image | 10000px × 10000px or more | 1024px × 1024px |
| Features | It is possible to show large area by connecting several image tiles | It is possible to quickly take and obtain image after staining tissue |

When it is possible to convert a tissue image obtained through such an endomicroscope system into an image similar to the staining type (color) of an H&E image and then provide the converted image to a medical technician, the medical technician would be able to conveniently perform pathologic diagnosis with reference to an image having a type similar to himself/herself.

Accordingly, the present disclosure discloses an AI model for pseudo coloring that converts images obtained through an endomicroscope system for digital biopsy to be close to the staining type of an H&E image.

Figure 12:
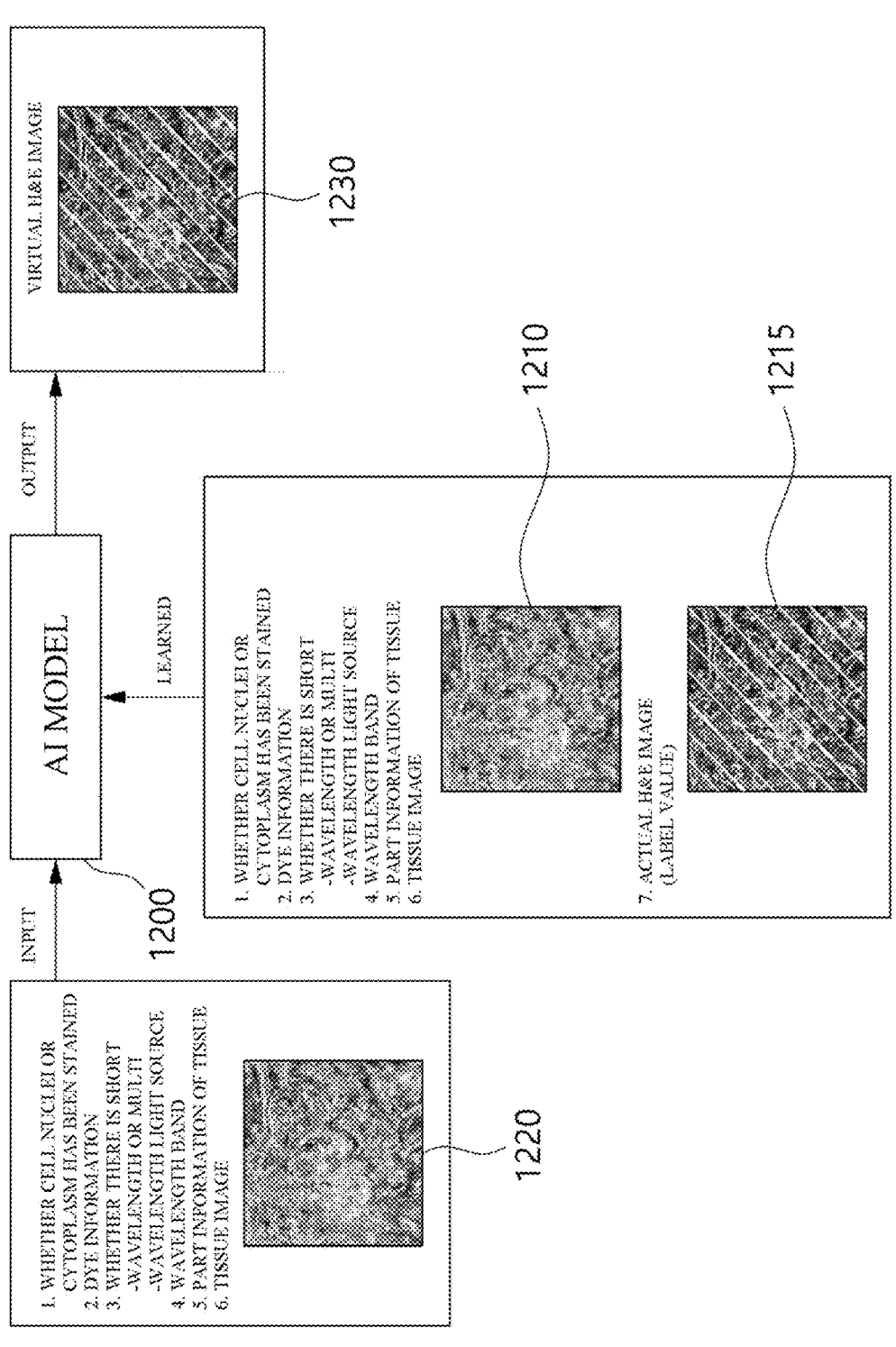
FIG. 12 is a diagram showing an AI model for pseudo coloring according to an embodiment of the present disclosure.

FIG. 12 is a diagram showing an AI model for pseudo coloring according to an embodiment of the present disclosure.

The AI model for pseudo coloring shown in FIG. 12 may be controlled by various types of electronic devices such as the endomicroscope system described above. For example, training the AI model for pseudo coloring to be described below and producing a virtual H&E image by inputting a tissue image may be performed by the controller 130 of the endomicroscope system. Further, the AI model for pseudo coloring may be implemented by a generative adversarial network (GAN) algorithm (e.g., algorithms such as pix-2-pix, cycle GAN, and style GAN) in the present disclosure. Meanwhile, the present disclosure is not limited thereto and the AI model for pseudo coloring may be implemented by various algorithms.

Referring to FIG. 12, an AI model 1200 may learn a first tissue image 1210 and an actual H&E image 1215 that is a labeling value for the first tissue image 310. The first tissue image 1210 may be a grayscale image or an RGB image. Meanwhile, the image that is used to train an AI model may mean a plurality of images in the present disclosure. The first tissue image 1210 for training that the AI model of the present disclosure learns and the actual H&E image 1215 may be images obtained through different methods for the same tissue. Alternatively, the first tissue image 1210 and the H&E image 1215 may mean image sets obtained for different tissues, respectively. That is, it is possible to learn conversions corresponding to each other using an image obtained through an endomicroscope system and an image obtained through H&E staining for the same tissue or it is also possible to train an AI model with a style change between a plurality of image sets obtained through different method for different tissues, respectively.

Further, the AI model 1200 may additionally learn the condition under which the first tissue image 1210 was obtained. For example, the condition may include at least one of whether a cell nucleus and/or cytoplasm has been stained, dye information, whether there is a short-wavelength or multi-wavelength light source, and a wavelength band. Table 1 described above may be referred for the condition under which the first tissue image 1210 was obtained. For example, referring to Table 1, a tissue to be observed through an endomicroscope system may be stained with a fluorescent dye that reacts to light having a first wavelength band (e.g., one of 400 to 410 nm, 480 to 500 nm, and 770 to 800 nm) or a fluorescent dye that reacts to light having a second wavelength band different from the first wavelength band. Further, the AI model 1200 may learn FOV information or probe type information (e.g., conical type or lensed type) as the condition under which the first tissue image 1210 was obtained. The endomicroscope system of the present disclosure may obtain the first tissue image 1210 by emitting light having the first wavelength band or the second wavelength band. Meanwhile, the first tissue image 1210 may be an image obtained directly from the endomicroscope system or an image obtained from another electronic device or medical device and stored in advance. Meanwhile, the first tissue image 1210 that is used for training the AI model 1200 may be obtained through various methods and the present disclosure is not limited thereto.

Further, the AI model 1200 may learn personal information of the examinee related to the first tissue image 1210. For example, the person information may include at least one of body information, sex information, or age information of the examinee.

The AI model 1200 may receive a second tissue image 1220 to be pseudo-colored. The second tissue image 1220 may be images obtained in a focused state. According to an embodiment, the second tissue image 1220 may be a grayscale image or an RGB image. Further, the size of the second tissue image may have a size smaller than 1 mm×1 mm, but application of the present disclosure is not limited to the size of images. Further, the AI model 1200 may additionally receive the condition under which the second tissue image 1220 was obtained. For example, the condition may include at least one of whether a cell nucleus and/or cytoplasm has been stained, dye information, whether there is a short-wavelength or multi-wavelength light source, and a wavelength band. Further, the AI model 1200 may receive FOV information or probe type information (e.g., conical type or lensed type) as the condition under which the second tissue image 1220 was obtained. Table 1 described above may be referred for the condition under which the second tissue image 1220 was obtained. For example, referring to Table 1, a tissue to be observed through an endomicroscope system may be stained with a fluorescent dye that reacts to light having a first wavelength band (e.g., one of 400 to 410 nm, 480 to 500 nm, and 770 to 800 nm) or a fluorescent dye that reacts to light having a second wavelength band different from the first wavelength band. The endomicroscope system of the present disclosure may obtain the second tissue image 1220 by emitting light having the first wavelength band or the second wavelength band. Meanwhile, the second tissue image 1220 may be an image obtained directly from the endomicroscope system or an image obtained from another electronic device or medical device and stored in advance. Meanwhile, the second tissue image 1220 that is used for training the AI model 1200 may be obtained through various methods and the present disclosure is not limited thereto.

Further, the AI model 1200 may receive personal information of the examinee related to the second tissue image 1220. For example, the person information may include at least one of body information, sex information, or age information of the examinee.

The AI model 1220 may output a third tissue image 1230 converted into an image similar to the staining type of an H&E image from the second tissue image 1220. The third tissue image that is output may be a virtual H&E image. The virtual H&E image may mean an image adjusted to have an impression of a color similar to a tissue image obtained through H&E staining. That is, the virtual H&E image may mean an image adjusted such that the color of each of parts corresponding to a nucleus and cytoplasm shows the color when stained with an H&E dye. For example, when the second tissue image 1220 is an image obtained by observing a tissue in which only nuclei are stained, a virtual H&E image may mean an image adjusted such that the color of parts corresponding to nuclei in the second tissue image 1220 shows the color when stained with hematoxylin (H) dye, and in this case, the virtual H&E image may be referred to as a virtual H image (or H-like image). As another example, when the second tissue image 1220 is an image obtained by observing a tissue in which only cytoplasm is stained, a virtual H&E image may mean an image adjusted such that the color of parts corresponding to cytoplasm in the second tissue image 1220 shows the color when stained with Eosin (E) dye, and in this case, the virtual H&E image may be referred to as a virtual E image (or E-like image).

According to the AI model for pseudo coloring described with respect to FIG. 12, medical technicians who use the endomicroscope system of the present disclosure may be provided with a virtual H&E image having a type familiar to themselves and may quickly and accurately perform pathologic diagnosis based on the virtual H&E image.

Meanwhile, variation of the staining type may occur during pseudo coloring. For example, deformation that regions assumed as nuclei in a tissue image are shown larger in a virtual H&E image or the boundaries between nuclei and cytoplasm are changed may occur.

When H&E staining is used, the nuclei of a malignant tumor usually enlarge in comparison to normal tissues, so overstaining may be generated. However, in pseudo coloring according to the present disclosure, a virtual H&E image in which a tissue may be misunderstood as being overstained even though it is normal because nuclei deform to be larger and darker may be generated.

In this case, medical technicians may be confused when performing pathologic diagnosis, so it may be advantageous that information (e.g., the size of a nucleus or the boundary between nucleus and cytoplasm regions) that is importantly used for pathologic diagnosis in a tissue image is not deformed during pseudo coloring. Alternatively, in contrast, it may be advantageous that a tissue determined as a malignant tumor is deformed as an overstaining image.

That is, in the case of performing pseudo coloring on an image of a specific tissue obtained through the endomicroscope system of the present disclosure, when an appropriate pseudo-coloring AI model may be selected in accordance with whether the specific tissue is normal or abnormal (e.g., cancer), it would be possible to obtain a virtual H&E image closer to an actual H&E image through the selected AI model.

In the previous embodiment, an AI model that receives a tissue image and generates medical diagnosis assistance information showing whether the tissue is normal or abnormal (e.g., cancer) was described. It would be possible to select an AI model for pseudo coloring in consideration of such medical diagnosis assistance information, that is, a diagnosis result on a tissue. Hereafter, FIG. 13 is referred to.

Figure 13:
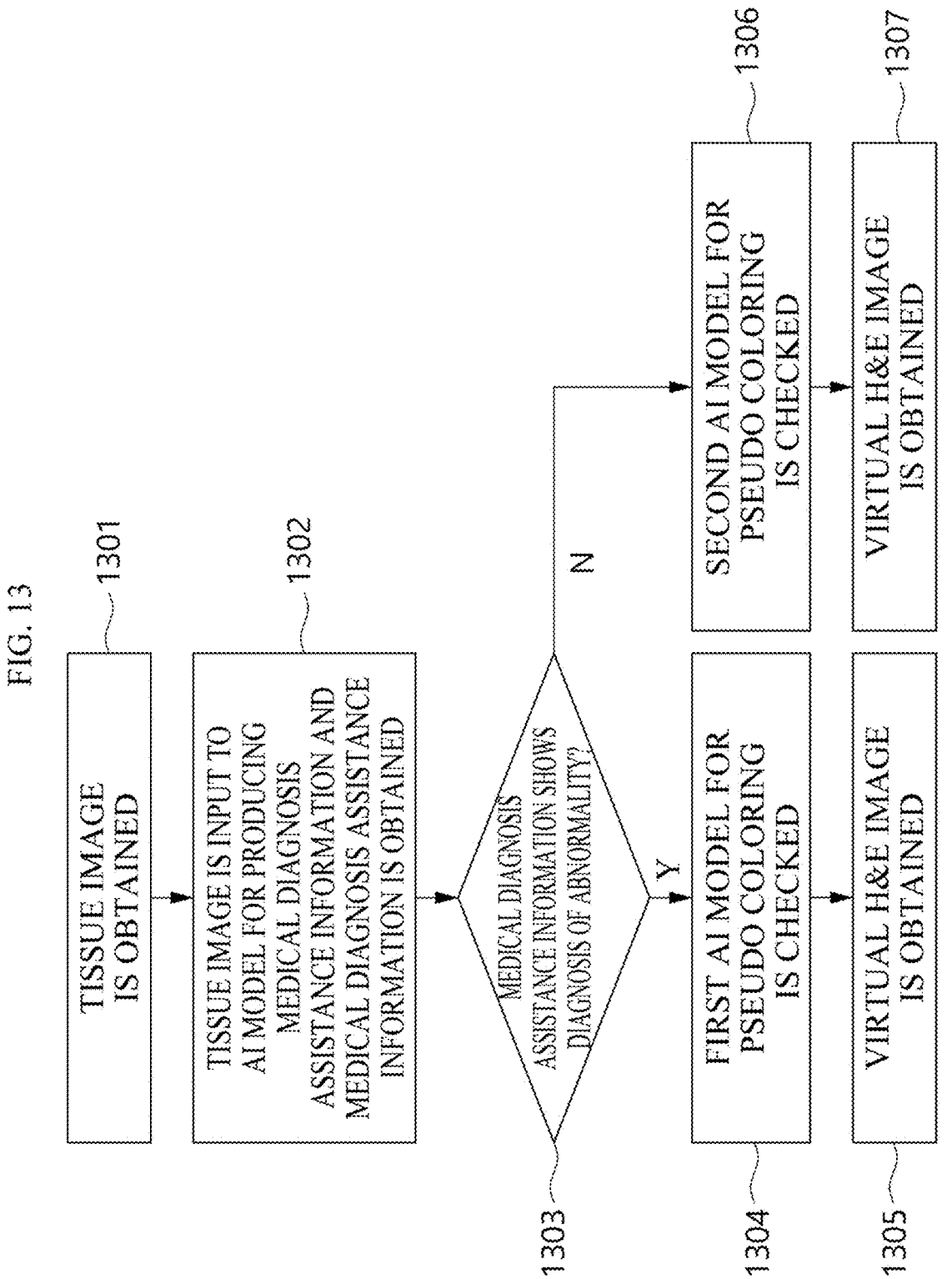
FIG. 13 is a diagram showing a method of selecting an AI model for pseudo coloring in accordance with a diagnosis result on a tissue according to an embodiment of the present disclosure.

FIG. 13 is a diagram showing a method of selecting an AI model for pseudo coloring in accordance with a diagnosis result on a tissue according to an embodiment of the present disclosure.

The steps shown in FIG. 13 may be performed by various types of electronic devices such as the endomicroscope system described above. For example, a method of selecting an AI model for pseudo coloring may be performed in accordance with a diagnosis result on a tissue by the controller 130 of the endomicroscope system.

Referring to FIG. 13, an endomicroscope system may obtain a tissue image in step 1301. The tissue image may be an image obtained from the endomicroscope system described above or an image selected from pre-stored images by a medical technician. Meanwhile, tissue images that are input to an AI model may be obtained through various methods and the present disclosure is not limited thereto. For example, the endomicroscope system of the present disclosure may obtain a tissue image in accordance with the description referring to FIG. 3.

In step 1302, the endomicroscope system may input the obtained tissue image into an AI model and may obtain medical diagnosis assistance information showing diagnosis of normality or abnormality (e.g., cancer) on the tissue related to the tissue image from the AI model. Further, the AI model that generates medical diagnosis assistance information in the present disclosure may be implemented by a convolution neural network (CNN) algorithm including Inception or Xception. Meanwhile, the present disclosure is not limited thereto and the AI model that generates medical diagnosis assistance information may be implemented by various algorithms. For example, the endomicroscope system of the present disclosure may obtain medical diagnosis assistance information on a tissue image in accordance with the description referring to FIG. 3. Further, the endomicroscope system of the present disclosure may identify whether it is possible to generate medical diagnosis assistance information on a tissue image in accordance with the description referring to FIG. 3, and may return to step 1301 and obtain a new tissue image when determining that it is impossible to generate medical diagnosis assistance information on the tissue image.

In step 1303, the endomicroscope system may identify whether the medical diagnosis assistance information obtained from the AI model shows diagnosis of abnormality (e.g., cancer).

When the medical diagnosis assistance information shows diagnosis of abnormality (e.g., cancer), the endomicroscope system may select a first AI model for performing pseudo coloring on a tissue image in step 1304. In step 1305, the endomicroscope system may input the tissue image into the first AI model and may obtain a virtual H&E image for the tissue image from the first AI model. For example, the first AI model may be an AI model that has learned a staining type that is expected when a tissue is abnormal (e.g., cancer). Further, the first AI model may be implemented by algorithms such as pix-2-pix, cycle GAN, and style GAN algorithms. Meanwhile, the present disclosure is not limited thereto and the first AI model for pseudo coloring may be implemented by various algorithms.

When the medical diagnosis assistance information shows diagnosis of normality, the endomicroscope system may select a second AI model for performing pseudo coloring on a tissue image in step 1306. Thereafter, in step 1307, the endomicroscope system may input the tissue image into the second AI model and may obtain a virtual H&E image for the tissue image from the second AI model. For example, the second AI model may be an AI model that has learned a staining type that is expected when a tissue is normal. Further, the second AI model may be implemented by algorithms such as pix-2-pix, cycle GAN, and style GAN algorithms. Alternatively, the second AI model may be implemented by an algorithm that is the same as or different from that of the first AI model. Meanwhile, the present disclosure is not limited thereto and the second AI model for pseudo coloring may be implemented by various algorithms.

According to another method, the endomicroscope system of the present disclosure may identify or select a pseudo coloring mode. For example, the endomicroscope system may identify or select a pseudo coloring mode based on whether an AI model that generates medical diagnosis assistance information has been trained in advance, whether an AI model for pseudo coloring for each diagnosis result has been trained, or selection by the user of the endomicroscope system.

When the endomicroscope system selects a first pseudo coloring mode, the endomicroscope system may generate a virtual H&E image by inputting a tissue image into an AI model for pseudo coloring without performing steps 1304 to 1307. For example, when an AI model that generates medical diagnosis assistance information has not been trained in advance or an AI model for pseudo coloring for each diagnosis result has not been trained, the endomicroscope system may select the first pseudo coloring mode.

When the endomicroscope system selects a second pseudo coloring mode, the endomicroscope system may generate a virtual H&E image by inputting a tissue image into an AI model for pseudo coloring in accordance with steps 1304 to 1307. For example, when an AI model that generates medical diagnosis assistance information and an AI model for pseudo coloring for each diagnosis result both have been trained in advance, the endomicroscope system may select the second pseudo coloring mode.

Although it is shown in FIG. 13 that steps 1301 to 1307 are sequentially performed, the present disclosure is not limited thereto. Some of steps 1301 to 1307 in FIG. 13 may be omitted or may be simultaneously performed.

Meanwhile, as described in FIGS. 4 to 6, an AI model that generates medical diagnosis assistance information may display an activated region that is the basis of determining cancer or normality in a tissue image. The present disclosure provides a method of gradually enlarging and displaying pseudo coloring from an activated region in a tissue image.

Figure 14:
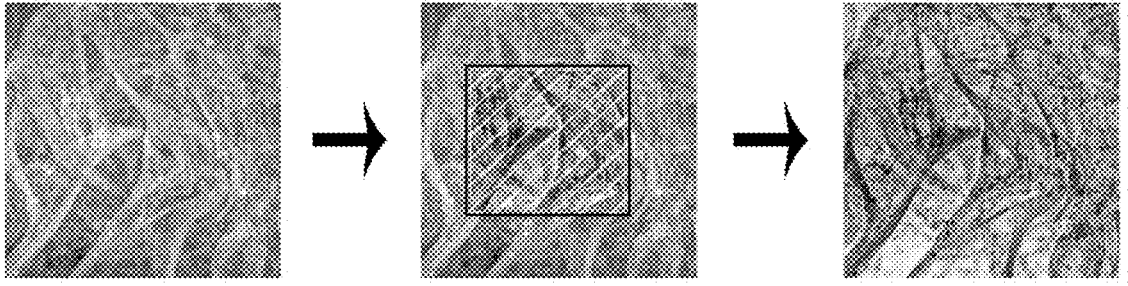
FIG. 14 is a diagram showing a process of gradually enlarging and displaying pseudo coloring from an activated region in a tissue image according to an embodiment of the present disclosure.

FIG. 14 is a diagram showing a process of gradually enlarging pseudo coloring from an activated region in a tissue image according to an embodiment of the present disclosure.

Referring to FIG. 14, an endomicroscope system may identify an activated region in an activation map displayed by an AI model that generates medical diagnosis assistance information on a tissue image. Further, the endomicroscope system may obtain a virtual H&E image for the tissue image through an AI model for pseudo coloring in accordance with the method described in FIG. 13. The endomicroscope system may display the process in which the tissue image is converted into the virtual H&E image on a display device or an external device by gradually enlarging color conversion from an activated region.

When a medical technician may see the process in which color conversion is gradually enlarged from an activated region and a tissue image is converted into a virtual H&E image in accordance with the method described in FIG. 14, it would be possible to draw attention of the medical technician and increase concentration of the medical technician on the important portion in the image.

As another method of selecting an AI model for pseudo coloring, the endomicroscope system of the present disclosure may select an AI model for pseudo coloring in accordance with a condition under which a tissue image was obtained.

Figure 15B:
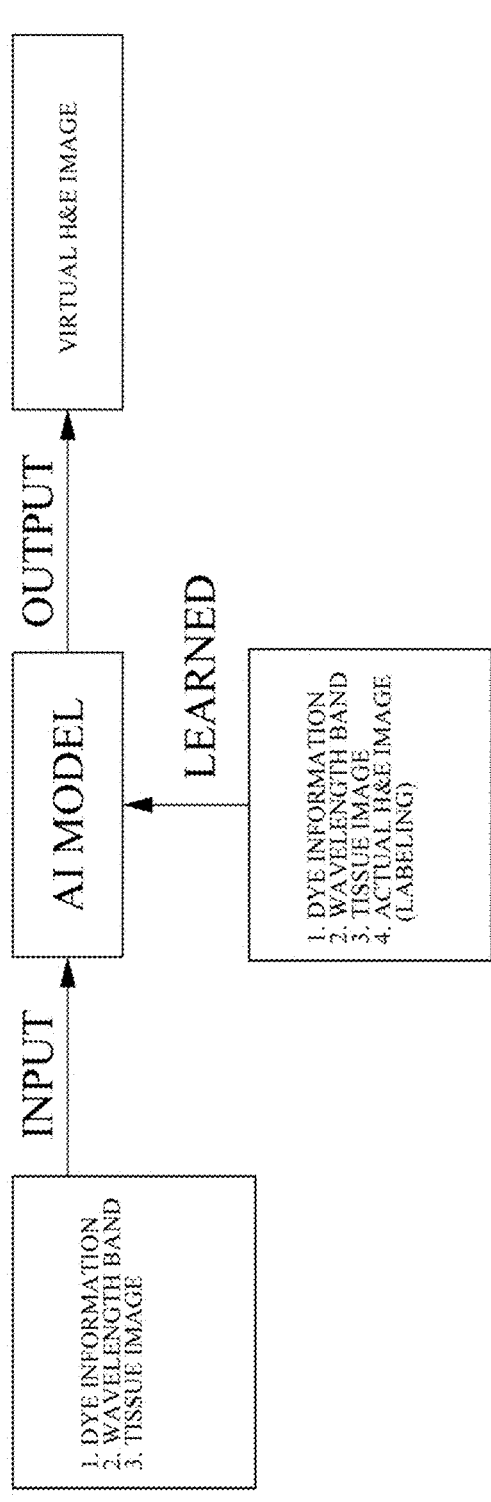

FIGS. 15A and 15B are diagrams showing an example of selecting an AI model for pseudo coloring in accordance with conditions for obtaining a tissue image through an endomicroscope system according to an embodiment of the present disclosure.

Referring to FIG. 15A, the endomicroscope system of the present disclosure may select an AI model for pseudo coloring in accordance with staining information of a tissue (e.g., whether cell nuclei or cytoplasm has been stained) or a laser information (e.g., operation information of the laser output module of the endomicroscope system) that is a condition under which a tissue image was obtained. Table 1 described above may be referred to for the staining information of a tissue and the laser information. Meanwhile, indexes given to an AI model 1-1 to an AI model 4 shown in FIG. 15A are provided to discriminate AI models that are changed in accordance with a user driving environment (e.g., input data, learning data, and/or desired output data) without intending to designate a specific AI model. That is, the given indexes are for discriminating AI models that a user can select to obtain a desired output image in accordance with the kind of an input image, and the AI model shown in the figure may mean different AI models that are discriminated from each other in accordance with input data and output data or may mean respective modes in one AI model of which the output is changed in accordance with modes selected by a user. The expression of AI model that is used in the present disclosure, which is an expression generally meaning algorithms or programs for implementing artificial intelligence, may mean an application or a source code that technicians having general knowledge in the field of the present disclosure can use to create desired output data, and/or a group of datasets for them.

For example, when only cytoplasm of a tissue has been stained (1 stain) and a tissue image has been obtained using a short-wavelength light source of a laser output module of an endomicroscope system, the endomicroscope system may select an AI model 1-1 to perform pseudo coloring on the tissue image. The endomicroscope system inputs the tissue image into the AI model 1-1 and the AI model 1-1 may output a virtual H&E image or a virtual E image by performing pseudo coloring on the tissue image. The AI model 1-1 may output a virtual H&E image by performing H&E like pseudo coloring on the tissue image. Alternatively, the AI model 1-1 may output a virtual E image by performing E-like pseudo coloring on the tissue image and the virtual E image may mean an image adjusted such that the color of the region corresponding to cytoplasm shows the color when stained with Eosin (E) dye.

As another example, when only cell nuclei of a tissue have been stained (1 stain) and a tissue image has been obtained using a short-wavelength light source of a laser output module of an endomicroscope system, the endomicroscope system may select an AI model 1-2 to perform pseudo coloring on the tissue image. The endomicroscope system inputs the tissue image into the AI model 1-2 and the AI model 1-2 may output a virtual H&E image or a virtual E image by performing pseudo coloring on the tissue image. The AI model 1-2 may output a virtual H&E image by performing H&E like pseudo coloring on the tissue image. Alternatively, the AI model 1-2 may output a virtual H image by performing H-like pseudo coloring on the tissue image and the virtual H image may mean an image adjusted such that the color of the region corresponding to cell nuclei shows the color when stained with Hematoxylin (H) dye.

As another example, when cytoplasm and cell nuclei of a tissue both have been stained (2 stain) and a tissue image has been obtained using a short-wavelength light source of a laser output module of an endomicroscope system, the endomicroscope system may select an AI model 2 to perform pseudo coloring on the tissue image. The endomicroscope system inputs the tissue image into the AI model 2 and the AI model 2 may output a virtual H&E image, a virtual H image, or a virtual E image by performing pseudo coloring on the tissue image. The AI model 2 may output a virtual H&E image by performing H&E like pseudo coloring on the tissue image. Alternatively, the AI model 2 may output a virtual H image by performing H-like pseudo coloring on the tissue image. Alternatively, the AI model 2 may output a virtual E image by performing E-like pseudo coloring on the tissue image.

As another example, when only cytoplasm of a tissue has been stained (1 stain) and a tissue image has been obtained using a multi-wavelength light source of a laser output module of an endomicroscope system, the endomicroscope system may select an AI model 3-1 to perform pseudo coloring on the tissue image. The endomicroscope system inputs the tissue image into the AI model 3-1 and the AI model 3-1 may output a virtual H&E image or a virtual E image by performing pseudo coloring on the tissue image. The AI model 3-1 may output a virtual H&E image by performing H&E like pseudo coloring on the tissue image. Alternatively, the AI model 3-1 may output a virtual E image by performing E-like pseudo coloring on the tissue image.

As another example, when only cell nuclei of a tissue have been stained (1 stain) and a tissue image has been obtained using a multi-wavelength light source of a laser output module of an endomicroscope system, the endomicroscope system may select an AI model 3-2 to perform pseudo coloring on the tissue image. The endomicroscope system inputs the tissue image into the AI model 3-2 and the AI model 3-2 may output a virtual H&E image or a virtual E image by performing pseudo coloring on the tissue image. The AI model 3-2 may output a virtual H&E image by performing H&E like pseudo coloring on the tissue image. Alternatively, the AI model 3-2 may output a virtual H image by performing H-like pseudo coloring on the tissue image.

As another example, when cytoplasm and cell nuclei of a tissue both have been stained (2 stain) and a tissue image has been obtained using a multi-wavelength light source of a laser output module of an endomicroscope system, the endomicroscope system may select an AI model 4 to perform pseudo coloring on the tissue image. The endomicroscope system inputs the tissue image into the AI model 4 and the AI model 4 may output a virtual H&E image, a virtual H image, or a virtual E image by performing pseudo coloring on the tissue image. The AI model 4 may output a virtual H&E image by performing H&E like pseudo coloring on the tissue image. Alternatively, the AI model 4 may output a virtual H image by performing H-like pseudo coloring on the tissue image. Alternatively, the AI model 4 may output a virtual E image by performing E-like pseudo coloring on the tissue image.

Meanwhile, the endomicroscope system of the present disclosure may generate a virtual H&E image by obtaining a virtual H image and a virtual E image from different AI models or a same AI model and combining them. For example, for a tissue image related to a tissue in which cytoplasm and cell nuclei are both stained, the endomicroscope system obtains a virtual E image through the AI model 3-1, obtains a virtual H image through the AI model 3-2, and then combines the virtual E image and the virtual H image, thereby being able to generate a virtual H&E image. Alternatively, for example, the endomicroscope system obtains a virtual H image and a virtual E image through the AI model 4 and combines them, thereby being able to generate a virtual H&E image. The combination of AI models that is used to combine a virtual H image and a virtual E image in order to generate a virtual H&E image is not limited to the example described above and it is apparent that the combination may be appropriately changed and used in accordance with the environment of a user (e.g., a dataset for training AI models, etc.).

The AI model 1-1, AI model 1-2, AI model 2, AI model 3-1, AI model 3-2, and AI model 4 shown in FIG. 15A may be different from each other. For example, the AI models may be implemented by different algorithms or the items of information that the AI models have learned in advance may be different.

Meanwhile, as described above, FIG. 15A shows an example in which an endomicroscope system selects an AI model for pseudo coloring in accordance with the condition under which a tissue image was obtained and the manes of the AI models shown in FIG. 15B are given only for the convenience of discrimination. Accordingly, the present disclosure is not limited thereto.

FIG. 15B shows the AI models shown in FIG. 15A.

Referring to FIG. 15B, the AI models shown in FIG. 15A each may learn a tissue image, an actual H&E image that is a labeling value for the tissue image, dye information (e.g., fluorescent dye information), and laser information (e.g., wavelength band information). Table 1 described above may be referred to for the dye information and the laser information.

For example, the AI model 1-1 may learn a tissue image, an actual H&E image or an actual E image (image obtained by observing a pathologic slide with only cytoplasm stained with Eosin (E)) that is a labeling value for the tissue image, fluorescent dye information staining the tissue, and wavelength band information of the laser. In this case, the actual E image may be an image obtained by processing the actual H&E image.

For example, the AI model 1-2 may learn a tissue image, an actual H&E image or an actual H image (image obtained by observing a pathologic slide with only cells stained with Hematoxylin (H)) that is a labeling value for the tissue image, fluorescent dye information staining the tissue, and wavelength band information of the laser. In this case, the actual H image may be an image obtained by performing image processing on the actual H&E image.

For example, the AI model 2 may learn a tissue image, an actual H&E image, an actual H image, or an actual E image that is a labeling value for the tissue image, fluorescent dye information staining the tissue, and wavelength band information of the laser. In this case, the actual H image and/or the actual E image may be an image obtained by performing image processing on the actual H&E image.

For example, the AI model 3-1 may learn a tissue image, an actual H&E image or an actual E image that is a labeling value for the tissue image, fluorescent dye information staining the tissue, and wavelength band information of the laser. In this case, the actual E image may be an image obtained by performing image processing on the actual H&E image.

For example, the AI model 3-2 may learn a tissue image, an actual H&E image or an actual H image that is a labeling value for the tissue image, fluorescent dye information staining the tissue, and wavelength band information of the laser. In this case, the actual H image may be an image obtained by performing image processing on the actual H&E image.

For example, the AI model 4 may learn a tissue image, an actual H&E image, an actual H image, or an actual E image that is a labeling value for the tissue image, fluorescent dye information staining the tissue, and wavelength band information of the laser. In this case, the actual H image and the actual E image may be an image obtained by performing image processing on the actual H&E image.

After learning, an AI model may receive a tissue image, dye information (e.g., fluorescent dye image), and laser information (e.g., wavelength band information). The tissue image that the AI model receives may be an image sorted as a high-quality image by an endomicroscope system or an image sorted as a high-quality image in accordance with selection by a user, and may be an image classified in accordance with dye information or FOV information.

For example, the AI model 1-1 may receive a tissue image, fluorescent dye information staining the tissue, and wavelength band information of the laser. This principle may be applied to the AI model 1-2, AI model 2, AI model 3-1, AI model 3-2, and AI model 4.

Thereafter, the AI model may generate a virtual H&E image for the received tissue image.

FIG. 16 is a diagram showing a method of selecting an AI model for pseudo coloring in accordance with conditions for obtaining a tissue image through an endomicroscope system according to an embodiment of the present disclosure.

The steps shown in FIG. 16 may be performed by various types of electronic devices such as the endomicroscope system described above. For example, a method of selecting an AI model for pseudo coloring may be performed in accordance with a condition for obtaining a tissue image by the controller 130 of the endomicroscope system.

Referring to FIG. 16, an endomicroscope system may obtain a tissue image in step 1601. The tissue image may be an image obtained from the endomicroscope system described above or an image selected from pre-stored images by a medical technician. Meanwhile, tissue images that are input to an AI model may be obtained through various methods and the present disclosure is not limited thereto. For example, the endomicroscope system of the present disclosure may obtain a tissue image in accordance with the description referring to FIG. 3.

In step 1602, the endomicroscope system may identify the condition under which the tissue image was obtained. For example, the endomicroscope system may identify staining information of a tissue (e.g., whether cell nuclei or cytoplasm has been stained) and laser information (e.g., whether there is a short-wavelength or multi-wavelength light source) as the condition under which the tissue image was obtained. Table 1 described above may be referred to for the staining information of a tissue and the laser information.

In step 1603, the endomicroscope system may identify or select a specific AI model from a plurality of AI models for pseudo coloring based on the condition under the tissue image was obtained. For example, the endomicroscope system may identify or select a specific AI model corresponding to the condition under the tissue image was obtained from the plurality of AI models. The plurality of AI models may be AI models trained as described in FIG. 15. Further, the plurality of AI models may be different from each other. For example, the plurality of AI models may be implemented by different algorithms or the items of information that the AI models have learned in advance may be different.

The endomicroscope system, in step 1604, inputs the tissue image and the condition under the tissue image was obtained into the AI model identified in step 1603, and in step 1605, the endomicroscope system may obtain a virtual H&E image (or a virtual H image or a virtual E image) for the tissue image from the AI model. For example, the endomicroscope system may identify and input dye information (e.g., fluorescent dye information) and laser information (e.g., wavelength band information) into the AI model as the condition under the tissue image was obtained. Table 1 described above may be referred to for the dye information of the tissue and the laser information.

According to another method, the endomicroscope system may identify or select a pseudo coloring mode. For example, the endomicroscope system may identify or select a pseudo coloring mode based on whether the AI models for respective conditions for obtaining a tissue image have been trained in advance or selection by the user of the endomicroscope system.

When the endomicroscope system selects a first pseudo coloring mode, the endomicroscope system may generate a virtual H&E image (or a virtual H image or a virtual E image) by inputting a tissue image into an AI model for pseudo coloring without performing steps 1603 to 1605. For example, when the AI models for respective conditions for obtaining a tissue image have not been trained in advance, the endomicroscope system may select the first pseudo coloring mode.

When the endomicroscope system selects a second pseudo coloring mode, the endomicroscope system may generate a virtual H&E image (or a virtual H image or a virtual E image) by inputting a tissue image into an AI model for pseudo coloring in accordance with steps 1603 to 1605. For example, when the AI models for respective conditions for obtaining a tissue image have been trained in advance, the endomicroscope system may select the second pseudo coloring mode.

Embodiments were described above with reference to the limited examples and drawings, but they may be changed and modified in various ways by those skilled in the art. For example, the described technologies may be performed in order different from the described method, and/or even if components such as the described system, structure, device, and circuit are combined or associated in different ways from the description or replaced by other components or equivalents, appropriate results may be accomplished.

Therefore, other implements, other embodiments, and equivalents to the claims are included in the following claims.

What is claimed is:

1. A confocal fluorescence endomicroscope system comprising:
a laser scanner;
a light receiver; and
a processor,
wherein the system is configured to determine whether to output medical diagnosis assistance information of an artificial intelligence model and to provide the information accordingly based on a condition for providing the medical diagnosis assistance information,
the processor configured to:
generate a first driving signal corresponding to a first axis and a second driving signal corresponding to a second axis different from the first axis;
generate a first image to detect excitation light generated by light emitted to a tissue to be examined from an end of the laser scanner operating based on the first driving signal and the second driving signal;
obtain the medical diagnosis assistance information including information on whether the tissue related to the first image is normal from the artificial intelligence model by inputting the first image into the artificial intelligence model;
identify an activated region related to the medical diagnosis assistance information on the first image;
determine that the condition for providing the medical diagnosis assistance information is satisfied in response to a size of the activated region at a specific color threshold being a threshold or more in an entire region and the number of closed loops of the activated region at the specific color threshold being less than or equal to a predetermined number;
provide the medical diagnosis assistance information on the first image when the condition is satisfied, and
do not provide the medical diagnosis assistance information on the first image in response to the condition being not satisfied,
wherein the predetermined number is a threshold indicating whether the medical diagnosis assistance information is suitable for pathological diagnosis generated by the artificial intelligence model,
wherein the specific color threshold is a pre-designated value, or a value selected by a user, and
wherein the artificial intelligence model is configured to:
receive, as a unified input set, both one or more tissue images and associated acquisition conditions for the one or more tissue images, wherein the associated acquisition conditions include a wavelength value of light and organ information, and wherein the one or more tissue images comprise the first image; and
generate, as an output, the medical diagnosis assistance information by performing a diagnostic analysis on the input set.

2. The confocal fluorescence endomicroscope system of claim 1, wherein the processor is configured to:
obtain new medical diagnosis assistance information by inputting again the first image into the artificial intelligence model,
identify an activated region related to the new medical diagnosis assistance information, and determine again whether the condition is satisfied, in response to the condition being not satisfied.

3. The confocal fluorescence endomicroscope system of claim 1, wherein the processor is configured to output the first image including the medical diagnosis assistance information to an external device in response to the condition being satisfied.

4. The confocal fluorescence endomicroscope system of claim 1, wherein the light includes first light having a first wavelength and second light having a second wavelength, and
wherein the processor is configured to:
generate a first assistant image about the tissue using the first light and generate a second assistant image about the tissue using the second light;
generate the first image by combining the first assistant image and the second assistant image; and
determine final medical diagnosis assistance information on the tissue using first medical diagnosis assistance information obtained by inputting the first assistant image into the artificial intelligence model, second medical diagnosis assistance information obtained by inputting the second assistant image into the artificial intelligence model, and third medical diagnosis assistance information obtained by inputting the first image into the artificial intelligence model.

5. The confocal fluorescence endomicroscope system of claim 4, wherein the first wavelength is included in one wavelength band of 400 nm to 410 nm, 480 nm to 500 nm, or 770 nm to 880 nm, and
wherein the second wavelength is included in another wavelength band different from the wavelength band including the first wavelength.

6. The confocal fluorescence endomicroscope system of claim 1, wherein the processor is configured to:
identify the organ information about the tissue;
identify the number of specific images corresponding to the organ information; and
determine medical diagnosis assistance information about the tissue using a plurality of images of the tissue in response to the plurality of images being obtained by the number of the specific images.

7. The confocal fluorescence endomicroscope system of claim 6, wherein the processor is configured to:
identify medical diagnosis assistance information on each of the plurality of images in response to the plurality of images being obtained by the number of the specific images while moving a probe including the laser scanner along a predetermined pattern; and
output a message that ignores medical diagnosis assistance information on one or more images, which relate to first type of medical diagnosis assistance information of the medical diagnosis assistance information about each of the plurality of images, or requests new medical diagnosis assistance information about the one or more images, in response to the number of the one or more images being a predetermined number or less and a minimum distance between the one or more images exceeds a predetermined distance.

8. The method of claim 1, wherein the medical diagnosis assistance information indicates whether cells or tissues in the one or more tissue images are normal or abnormal.

9. The method of claim 1, wherein the artificial intelligence model is configured to use at least tissue images labeled with diagnostic outcome as training data.

10. A method of providing medical diagnosis assistance information using a confocal fluorescence endomicroscope system, wherein the confocal fluorescence endomicroscope system is configured to determine whether to output the medical diagnosis assistance information of an artificial intelligence model and to provide the information accordingly based on a condition for providing the medical diagnosis assistance information, the method comprising:

generating a first driving signal corresponding to a first axis and a second driving signal corresponding to a second axis different from the first axis;

generating a first image to detect excitation light generated by light emitted to a tissue to be examined from an end of a laser scanner operating based on the first driving signal and the second driving signal;

inputting the first image into the artificial intelligence model;

obtaining the medical diagnosis assistance information including information on whether the tissue related to the first image is normal from the artificial intelligence model;

identifying an activated region related to the medical diagnosis assistance information on the first image;

determining that the condition for providing the medical diagnosis assistance information is satisfied in response to a size of the activated region at a specific color threshold being a threshold or more in an entire region and the number of closed loops of the activated region at the specific color threshold being less than or equal to a predetermined number;

providing the medical diagnosis assistance information on the first image when the condition is satisfied; and not providing the medical diagnosis assistance information on the first image in response to the condition being not satisfied, wherein the predetermined number is a threshold indicating whether the medical diagnosis assistance information is suitable for pathological diagnosis generated by the artificial intelligence model, wherein the specific color threshold is a pre-designated value or a value selected by a user, and wherein the artificial intelligence model is configured to:

receive, as a unified input set, both one or more tissue images and associated acquisition conditions for the one or more tissue images, wherein the associated acquisition conditions include a wavelength value of light and organ information, and wherein the one or more tissue images comprise the first image; and generate, as an output, the medical diagnosis assistance information by performing a diagnostic analysis on the input set.

11. The method of claim 10, further comprising:

in response to the condition being not satisfied, obtaining new medical diagnosis assistance information by inputting again the first image into the artificial intelligence model;

identifying an activated region related to the new medical diagnosis assistance information; and determining again whether the condition is satisfied.

12. The method of claim 10, further comprising outputting the first image including the medical diagnosis assistance information to an external device when the condition is satisfied.

13. The method of claim 10, wherein the light includes first light having a first wavelength and second light having a second wavelength, and the method further comprising:

generating a first assistant image about the tissue using the first light and generate a second assistant image about the tissue using the second light;

generating the first image by combining the first assistant image and the second assistant image; and determining final medical diagnosis assistance information on the tissue using first medical diagnosis assistance information obtained by inputting the first assistant image into the artificial intelligence model, second medical diagnosis assistance information obtained by inputting the second assistant image into the artificial intelligence model, and third medical diagnosis assistance information obtained by inputting the first image into the artificial intelligence model.

14. The method of claim 13, wherein the first wavelength is included in one wavelength band of 400 nm to 410 nm, 480 nm to 500 nm, or 770 nm to 880 nm, and wherein the second wavelength is included in another wavelength band different from the wavelength band including the first wavelength.

15. The method of claim 10, further comprising:

identifying the organ information about the tissue;

identifying the number of specific images corresponding to the organ information; and determining medical diagnosis assistance information on the tissue using a plurality of images of the tissue in response to the plurality of images being obtained by the number of the specific images.

16. The method of claim 15, further comprising:

identifying medical diagnosis assistance information on each of the plurality of images in response to the plurality of images being obtained by the number of the specific images while moving a probe including the laser scanner along a predetermined pattern; and outputting a message that ignores medical diagnosis assistance information on one or more images, which relate to first type of medical diagnosis assistance information of the medical diagnosis assistance information about each of the plurality of images, or requests new medical diagnosis assistance information about the one or more images, in response to the number of the one or more images being a predetermined number or less and a minimum distance between the one or more images exceeds a predetermined distance.

* * * * *